US008642274B2

(12) United States Patent
Harrop et al.

(10) Patent No.: US 8,642,274 B2
(45) Date of Patent: Feb. 4, 2014

(54) IMMUNOTHERAPEUTIC METHOD

(75) Inventors: Richard Harrop, Oxford (GB); William Shingler, Oxford (GB); Stuart Naylor, Oxford (GB); Michael McDonald, Guildford (GB)

(73) Assignee: Oxford Biomedica, Inc., Oxford (GB)

( * ) Notice: Subject to any disclaimer, the term of this patent is extended or adjusted under 35 U.S.C. 154(b) by 0 days.

(21) Appl. No.: 12/503,512

(22) Filed: Jul. 15, 2009

(65) Prior Publication Data

US 2010/0124534 A1    May 20, 2010

Related U.S. Application Data

(60) Provisional application No. 61/081,024, filed on Jul. 15, 2008, provisional application No. 61/143,600, filed on Jan. 9, 2009, provisional application No. 61/182,525, filed on May 29, 2009.

(51) Int. Cl.
*G01N 33/53* (2006.01)
(52) U.S. Cl.
USPC .......................................................... 435/7.1
(58) Field of Classification Search
None
See application file for complete search history.

(56) References Cited

U.S. PATENT DOCUMENTS

| | | | |
|---|---|---|---|
| 6,852,703 B1 | 2/2005 | Kingsman et al. |
| 7,074,909 B2 | 7/2006 | Kingsman et al. |
| 7,148,035 B1 | 12/2006 | Carroll et al. |
| 7,276,488 B2 | 10/2007 | Kingsman et al. |
| 7,402,066 B2 | 7/2008 | Liao |
| 7,514,546 B2 | 4/2009 | Kingsman et al. |
| 7,531,648 B2 | 5/2009 | Kingsman et al. |
| 7,541,044 B2 | 6/2009 | Harrop et al. |
| 7,601,698 B2 | 10/2009 | Carroll et al. |
| 7,615,612 B2 | 11/2009 | Carroll et al. |
| 7,635,687 B2 | 12/2009 | Kingsman et al. |
| 7,659,383 B2 | 2/2010 | Myers et al. |
| 7,666,669 B2 | 2/2010 | Carroll et al. |
| 7,718,627 B2 | 5/2010 | Kingsman et al. |
| 8,084,249 B2 | 12/2011 | Kingsman et al. |
| 2005/0118597 A1 | 6/2005 | Carroll et al. |
| 2005/0123918 A1 | 6/2005 | Carroll et al. |
| 2009/0047307 A1 | 2/2009 | Harrop et al. |
| 2010/0040539 A1 | 2/2010 | Kingsman et al. |
| 2011/0052577 A1 | 3/2011 | Kingsman et al. |

FOREIGN PATENT DOCUMENTS

| | | |
|---|---|---|
| EP | 0707071 A1 | 4/1996 |
| WO | WO-00/63406 A2 | 10/2000 |
| WO | WO-01/17537 A2 | 3/2001 |
| WO | WO-2007/034188 A2 | 3/2007 |
| WO | WO-2008/128251 A1 | 10/2008 |

OTHER PUBLICATIONS

Harrop et al (Clin Cancer Res, 2006, 12(11): 3416-3424).*
Amato (Expert Opin Ther, 2007, 7(9): 1463-1469).*
Amato et al., "Vaccination of Prostate Cancer Patients With Modified Vaccinia Ankara Delivering the Tumor Antigen 5T4 (TroVax)," *J. Immunother*, 31(6):577-585 (2008).
Amato et al., "Vaccination of Renal Cell Cancer Patients with Modified Vaccinia Ankara Delivering Tumor Antigen 5T4 (TroVax) Administered wtih Interleukin 2: A Phase II Trial," *Cancer Therapy: Clinical*, 14(22):7504-7510 (2008).
Elkord et al., "A MVA-based Vaccine Targeting the Oncofetal Antigen 5T4 in Patients Undergoing Surgical Resection of Colorectal Cancer Liver Metastases," *J. Immunother*, 31(9):820-829 (2008).
Harrop et al., "Vaccination of Colorectal Cancer Pateitns with Modified Vaccinia Ankara Delivering the Tumor Antigen 5T4 (TroVax) Induces Immune Responses which Correlate with Disease Control: A Phase I/II Trial," *Clin. Cancer Res.*, 12(11):3416-3424 (2006).
Harrop et al., "Vaccination of Colorectal Cancer Patients with Modified Vaccinia Ankara Encoding the Tumor Antigen 5T4 (TroVax) Given Alongside Chemotherapy Induces Potent Immune Responses," *Clin. Cancer Res.*, 13(15):4487-4494 (2007).
Harrop et al., "Vaccination of colorectal cancer patients with TroVax given alongside chemotherapy (5-fluorouracil, leukovorin and irinotecan) is safe and induces potent immune responses," *Cancer Immunol Immunother*, 57:977-986 (2008).
Li et al., "A sample size adjustment procedure for clinical trials based on conditional power," *Biostatistics*, 3(2):277-287 (2002).
International Search Report for PCT/GB2009/001748, dated Dec. 17, 2009.
International Preliminary Report on Patentability for PCT/GB2009/001748, dated Jan. 18, 2011.

* cited by examiner

*Primary Examiner* — Sean Aeder
(74) *Attorney, Agent, or Firm* — Marshall, Gerstein & Borun LLP

(57) ABSTRACT

The present invention provides a method of monitoring the efficacy of an immunotherapy in a mammalian subject, wherein the subject has been administered an immunotherapy, wherein the immunotherapy comprises a viral vector containing a polynucleotide encoding an antigen, wherein the viral vector is capable of transducing cells in the mammalian subject to cause the cells to express the antigen; the method comprising:
(b) measuring, from a biological sample isolated from the subject, an immune response of the subject to the antigen and comparing the immune response of the subject to the antigen to a reference measurement of immune response to the antigen;
(c) measuring, from a biological sample isolated from the subject, an immune response of the subject to the viral vector and comparing the immune response of the subject to the viral vector to a reference measurement of immune response to the viral vector; and
(d) determining efficacy based on the comparisons of (b) and (c), wherein an elevated immune response to the antigen and a reduced immune response to the viral vector are indicative of an effective immunotherapy.

8 Claims, 8 Drawing Sheets

IMMUNOTHERAPEUTIC METHOD

CROSS REFERENCE TO RELATED APPLICATIONS

The present application claims the benefit of priority of U.S. Provisional Application Nos. 61/081,024; 61/143,600 and 61/182,585, filed Jul. 15, 2008; Jan. 9, 2009 and May 29, 2009, respectively. The disclosure of each priority application is incorporated herein by reference in its entirety.

FIELD OF THE INVENTION

The application concerns immunotherapeutic compositions and methods for treating cancer patients with such compositions.

BACKGROUND OF THE INVENTION

Tumor cells are notoriously poor immunogens despite the fact that many antigens that are over-expressed or unique to tumor cells (tumor-associated antigens) have been identified. The reasons for this apparent lack of immunogenicity may be that cancer antigens are generally not presented to the immune system in a micro-environment that favors the activation of immune cells which would lead to the killing of the tumor cells. Although no single known mechanism can explain poor tumor immunogenicity in all experimental models studied, the molecular basis can be separated conceptually into distinct groupings: i) lack of expression of co-stimulatory molecules essential for effective immune induction, ii) production of immuno-inhibitory substances and iii) variability in the expression of antigen by tumors.

Much progress has been made in the identification of tumor-associated antigens (TAA) that are potentially useful in the development of recombinant anti-cancer vaccines. TAAs can be divided into three major categories: i) non-self viral antigens e.g. E6/E7 from human papilloma virus (HPV), ii) altered self-antigens e.g. MUC-1 and iii) non-mutated self-antigens e.g. 5T4 and carcinoembryonic antigen (CEA).

Vaccinia virus (VV), a member of the poxvirus family, has been developed as a recombinant expression vector for the genetic delivery of antigens. Animals injected with a recombinant VV (rVV) have been shown to produce both antibody and CTL responses to the exogenous proteins. In contrast to tumor cells VV infection appears to create an optimal environment for the induction of an efficacious immune response. Recombinant VV expressing murine homologues of TAA, which are classed as self-antigens, have also been shown to induce TAA specific immune responses in murine models, illustrating that such constructs are potentially able to overcome immune tolerance to self-antigens. In vivo models demonstrate that such responses are able to prevent tumor establishment and in some cases are able to actively treat established tumors. These data also indicate that it is possible to turn an anti-viral response into an anti-cancer response by presenting a TAA in the context of viral antigens.

Recombinant VV vectors expressing the self-antigen CEA have been constructed and have been evaluated for toxicity and to a lesser extent efficacy in late stage colorectal cancer. Such rVV vectors were well tolerated and both antibody and cell mediated immune responses to the self-antigen CEA were reported. Lack of tumor response data in these trials may be due to the patient population which had very advanced tumors and had already failed prior chemotherapy. To date over 700 people have been vaccinated with rVV and other poxviruses expressing TAAs in a spectrum of cancer immunotherapy clinical trials. There have been no reports of toxicity either from the virus itself or as a result of the immune response induced to the TAA beyond local injection site reactions and transient pyrexia. However, there remains a need for suitable methods for assessing efficacy of immunotherapy and suitable clinical markers that can guide therapeutic methods.

SUMMARY

The invention provides materials and methods that address one or more needs in the fields of cancer therapy, immunotherapy, or related fields.

Some aspects of the invention relate to materials and methods for monitoring the efficacy of an immunotherapy. Improved monitoring permits improvement of therapy for individual subjects; and more rapid determination of which subjects benefit from the therapy. Subjects obtaining less benefit can more quickly be given modified or different therapeutic regimens.

One variation of the invention is a method of monitoring efficacy of immunotherapy comprising:

(a) administering an immunotherapy to a mammalian subject, wherein the immunotherapy comprises a viral vector containing a polynucleotide encoding an antigen, wherein the viral vector is capable of transducing cells in the mammalian subject to cause the cells to express the antigen;

(b) measuring an immune response of the subject to the antigen, and comparing the immune response to the antigen of the subject to a reference measurement of immune response to the antigen;

(c) measuring an immune response of the subject to the viral vector and comparing the immune response of the subject to the viral vector to a reference measurement of immune response to the viral vector;

(d) determining efficacy based on the comparisons of (b) and (c), wherein an elevated immune response to the antigen and a reduced immune response to the viral vector are indicative of an effective immunotherapy.

Another variation of the invention is a method of monitoring efficacy of an immunotherapy in a mammalian subject, wherein the subject has been administered an immunotherapy, wherein the immunotherapy comprises a viral vector containing a polynucleotide encoding an antigen, wherein the viral vector is capable of transducing cells in the mammalian subject to cause the cells to express the antigen; the method comprising:

(a) measuring, from a biological sample isolated from the subject, an immune response of the subject to the antigen and comparing the immune response to the antigen of the subject to a reference measurement of immune response to the antigen;

(b) measuring, from a biological sample isolated from the subject, an immune response of the subject to the viral vector and comparing the immune response of the subject to the viral vector to a reference measurement of immune response to the viral vector;

(c) determining efficacy based on the comparisons of (b) and (c), wherein an elevated immune response to the antigen and a reduced immune response to the viral vector are indicative of an effective immunotherapy.

Still another variation of the invention is a method of determining probability of survival of a mammalian subject over a period of time, wherein the subject has been administered an immunotherapy, wherein the immunotherapy comprises a viral vector containing a polynucleotide encoding an antigen, wherein the viral vector is capable of transducing cells in the mammalian subject to cause the cells to express the antigen; the method comprising:

(a) measuring, from a biological sample isolated from the subject, an immune response of the subject to the antigen following a first vaccination and comparing the immune response to the antigen of the subject to a reference measurement of immune response to the antigen;

(b) measuring, from a biological sample isolated from the subject, an immune response of the subject to the viral vector following a first vaccination and comparing the immune response of the subject to the viral vector to a reference measurement of immune response to the viral vector;

(c) determining probability of survival of the mammalian subject based on whether the comparison in (a) and the comparison in (b) is above or below a median value.

This variation of the invention can be repeated following a second vaccination. In related aspects, this variation of the invention can be repeated following a third, fourth, fifth, sixth, seventh, eighth, ninth, tenth, eleventh, twelfth, thirteenth, fourteenth, fifteenth, sixteenth, seventeenth, eighteenth, nineteenth, twentieth or more vaccination.

The probability determination may be an element to deciding whether to continue the patient on the immunotherapy, supplement with a different standard of care therapy, or discontinue the immunotherapy entirely. Methods that include such steps also are an aspect of the invention.

Other aspects of the invention include improved immunotherapeutic methods. Information provided herein about characteristics of subjects that obtain greater or lesser benefit from immunotherapies provides indications of improved therapeutic regimens.

For example, another embodiment of the invention is a method of immunotherapy comprising:

(a) administering an immunotherapy to a mammalian subject, wherein the immunotherapy comprises a viral vector containing a polynucleotide encoding an antigen, wherein the viral vector is capable of transducing cells in the mammalian subject to cause the cells to express the antigen;

(b) measuring an immune response of the subject to the antigen and to the viral vector after the administering step; and (c) repeating step (a) until a measurable immune response to the antigen is achieved.

Such a method may, optionally, further comprise (d) immunizing the subject having a measurable immune response to the antigen with a maintenance immunotherapy that is free from the viral vector. Exemplary maintenance immunotherapies include compositions that include the protein antigen itself; or fragments or epitopes of the antigen; or vectors (other than the original viral vector) for delivering a transgene that encodes the antigen (e.g., plasmid or liposomal vectors).

A related aspect of the invention is a viral vector containing a polynucleotide encoding an antigen for use in an immunotherapy, wherein the viral vector is capable of transducing cells in the mammalian subject to cause the cells to express the antigen; and wherein the immunotherapy comprises repeated administrations of the viral vector until a measurable immune response of the subject to the antigen is achieved, whereupon administrations of the viral vector is ceased. The immunotherapy may further include at least one administration of the antigen following cessation of administrations of the viral vector, to maintain or enhance the immune response of the subject.

The present invention also provides the use of a viral vector in the manufacture of a medicament for use in an immunotherapy, wherein the viral vector contains a polynucleotide encoding an antigen and is capable of transducing cells in the mammalian subject to cause the cells to express the antigen; and wherein the immunotherapy comprises repeated administrations of the viral vector until a measurable immune response of the subject to the antigen is achieved, whereupon administrations of the viral vector is ceased.

In a further embodiment there is provided a method of immunotherapy comprising: (a) measuring an immune response to an antigen in a mammalian subject to determine a reference response; (b) administering an immunotherapy to the subject wherein the immunotherapy comprises a viral vector containing a polynucleotide encoding the antigen, wherein the viral vector is capable of transducing cells in the mammalian subject to cause the cells to express the antigen; (c) measuring an immune response to the antigen in the subject after step (b); and (d) repeating steps (b) and (c) until a measurable increase in the immune response to the antigen relative to the reference immune response is achieved. For example, the increase in immune response may comprise a 2-, 3-, 4-, 5-, 10-, or 20-fold increase above reference. In certain specific aspects, the immunotherapy is a 5T4 immunotherapy (e.g., administration of MVA-5T4, TroVax®) and the immune response measured is a 5T4 specific antibody titer or a 5T4 specific T cell response.

In still a further embodiment there is provided, a method of identifying a subject which is a candidate for further immunotherapy comprising: (a) measuring an immune response to an antigen (e.g., a therapeutic antigen) in a subject to determine a reference response; (b) administering an immunotherapy to the subject one or more times; (c) measuring an immune response to the antigen in the subject after step (b); and (d) comparing the immune response determined in step (c) to the reference response wherein a subject having an increased immune response relative to the reference response is a candidate for further administration of immunotherapy. For instance, in some aspects, step (b) comprises administering an immunotherapy 2, 3, 4, 5 or more times. As demonstrated in Example 5 below, two, three or four courses of MVA-5T4 immunotherapy provide excellent points for measuring the efficacy of the immunotherapy. In some variation of the invention, a subject that is exhibiting insufficient evidence of an immune response after two, three or four courses may be recommended to discontinue MVA-5T4 immunotherapy and/or undertake a different standard of care therapy or different immunotherapy to attempt to provide more effective therapeutic intervention. In a specific aspect, a candidate for further immunotherapy may be defined as a subject having at least about a 4-fold increase in 5T4 antibody titer after 4 administrations of MVA-5T4 (TroVax®). In certain cases, a further immunotherapy comprises administration of an immunotherapy at a different dose or on different schedule than an initial immunotherapy. For example, in certain aspects, a further immunotherapy is administered in a dose/schedule sufficient to maintain an immune response that is at least about 2-, 3-, 4-, 5- or 10-fold above a reference baseline response. In certain aspects, a subject having little or no increase immune response relative to the reference response is not administered further immunotherapy and/or is administered a secondary therapy such as chemotherapy, a radiotherapy or a surgical therapy. In certain specific cases, a subject having little increase in an immune response is defined as a subject having less that about a 4-, 3- or 2-fold increase in immune response over reference.

Moreover, in certain aspects, a method of identifying a subject which is a candidate for further immunotherapy may comprise (a) measuring an immune response a therapeutic antigen (e.g., 5T4 antigen) and a vector antigen (e.g., MVA)

in a subject to determine reference responses; (b) administering an immunotherapy to the subject one or more times; (c) measuring an immune response to the therapeutic antigen and the vector antigen in the subject after step (b); and (d) comparing the immune responses determined in step (c) to the reference responses wherein a subject having an increased therapeutic antigen immune response relative to the reference response is a candidate for further administration of immunotherapy and a subject a subject having an increased vector antigen immune response relative to the reference vector antigen response is not a candidate for further administration of immunotherapy.

The present invention also provides a method of monitoring the efficacy of an immunotherapy by (a) measuring an immune response to an antigen in a mammalian subject to determine a baseline response; (b) administering an immunotherapy to the subject wherein the immunotherapy comprises a viral vector containing a polynucleotide encoding the antigen, wherein the viral vector is capable of transducing cells in the mammalian subject to cause the cells to express the antigen; (c) measuring an immune response to the antigen in the subject; and (d) comparing the immune response to the antigen relative to the baseline immune response.

As used herein measuring an immune response may comprise measuring a humoral or a cell mediated immune response to an antigen, a viral vector or both. For example, measuring an immune response may comprise measuring a CTL response, a helper T cell response or an antibody response. Methods for measuring both cell mediated and humoral immune responses are well known and a variety of commercially available assay systems are available. In some aspects measuring an immune response comprises obtaining one or more samples from a subject, such as a blood or serum sample. In certain aspects, samples from a subject may include a reference sample (prior to administering an immunotherapy to the subject) and one or more samples that are collected after administration of an immunotherapy. Moreover, in certain aspects measuring an immune response in a sample may comprise obtaining a measurement of an immune response from a sample. For example, a sample may be obtained from a subject and the sample(s) provided to a third party for measurement and reporting of an immune response thereby obtaining a measurement of an immune response.

In certain aspects measuring an immune response comprises measuring an antibody response. For example, the concentration of antigen specific antibodies in a sample may be determined by methods such as enzyme-linked immunosorbent assay (ELISA). In some aspects, a sample is contacted with an immobilized antigen of interest (e.g., a 5T4 antigen or poxvirus antigen or a portion thereof) and the amount of antibody that binding to the antigen is detected (e.g., by contacting the bound antibody with a second antibody having a detectable marker or signaling agent). Alternatively, in some aspects, antibodies from a sample may be immobilized and amount of antigen specific antibodies detected by contacting the immobilized antibodies with a labeled antigen (e.g., labeled 5T4 antigen).

In still further aspects measuring an immune response may comprise measuring a cell-mediated immune response. For example, antigen and/or epitope specific T cells may be detected by contacting a sample comprising T cells with an epitope capable of presentation to a T cell and detecting T cell activation or cytokine production for example using ELISPOT assay, intracellular cytokine staining, flow cytometry or by using MHC-epitope tetramers or pentamers. In some further cases, cytotoxic T cell activity in sample may be measured, for example, by a chromium release assay. In still further aspects, measuring a cell mediated immune response may comprise measuring a cell mediated immune response to two or more T cell epitopes of an antigen. A number of 5T4 antigen T-cell epitopes known see e.g., U.S. Patent Publication Nos. 20050123918 and 20050118597, incorporated herein by reference.

In some variations, an immune response may be compared to a reference immune response such as an average or median measurement calculated from a plurality mammalian subjects that received the administering of the immunotherapy. Where the reference is an average or median, a measurement for the immune response above the reference measurement is scored as elevated and a measurement below the reference measurement is scored is reduced. In other variations, a measurement that statistically varies from the median or mean by a suitable significant amount (e.g., 1 or 1.5 or 2 standard deviations; or by a "p-value" or other statistical measure of significance) is scored as elevated or reduced.

In other variations, a reference immune response may be a baseline measurement or any other absolute measurement for a particular assay tool. In such variations, an elevated immune response or a reduced immune response may represent values that are a certain multiple or fraction of the reference value. In the case an immune response to 5T4 antigen for example, a reference measurement may be an average immune response for subject who is untreated, a responder to an immunotherapy or a non-responder to an immunotherapy or median immune response. Thus, in certain aspects, determining a 5T4 immune response comprises measuring a 5T4 immune response and comparing the response to a reference measurement. Likewise, determining an MVA immune response, in certain aspects, comprises measuring an MVA immune response and comparing the response to a reference measurement. For example, an elevated immune response may be defined as an immune response which is 2-, 3-, 4-, 5-, 6-, 7-, 8-, 9-, 10-, 15-, 20- or 50-fold above a baseline reference immune response.

Some aspects of the invention involve screening for or determining the presence of a measurable immune response. Measurable may be defined as an immune response greater than a baseline response, and more preferably at least about 2, 5, 10, 50, 100 or 1000 fold over a baseline response. In cases where there is no measurable baseline response, a baseline response may be defined as the lower detection limit of the assay used to measure the immune response. Hence, in certain aspects there is provided a method of administering immunotherapy to a mammalian subject for whom immunotherapy is determined to be effective by the measurement of an immune response to an antigen, a viral vector or both.

It is contemplated that the methods of the invention are suitable and applicable for all viral vectors adaptable for delivery of an exogenous gene to a mammalian cell for expression of the gene in the cell. A variety of viral vectors may be employed as disclosed herein. In some preferred aspects, viral vectors are replication deficient. Furthermore, as detailed above, a viral vector may preferably comprise poxvirus such as a vaccinia viral vector. A variety of vaccinia viral vectors are known in the art in certain aspects a vaccinia viral vector for use herein may be a modified vaccinia Ankara (MVA) virus. Thus, according to the methods disclosed here in administration step that comprise it least three administrations of a viral vector to a subject. Conversely, an administration step may comprise no more than 13 administrations the viral vector to a subject.

In some aspects immunotherapeutic methods concern a maintenance immunotherapy that does not comprise the viral vector. For instance, the maintenance immunotherapy comprises a composition comprising the antigen, or at least one epitope thereof, and an adjuvant or carrier. For example, a maintenance immunotherapy may comprise a plasmid that contains a nucleotide sequence that encodes the antigen, operably linked to an expression control sequence to permit expression of the antigen in cells of the mammalian subject.

Likewise, methods disclosed herein are applicable to immunotherapy utilizing a variety of antigens. In certain aspects, an antigen as defined herein comprises at least one tumor antigen such as the tumor antigens listed in the detailed description below. For example, the tumor antigen may comprise a 5T4 antigen. 5T4 antigen and viral vectors comprising 5T4 have been previously described for examples in U.S. Pat. No. 7,148,035, incorporated herein by reference.

The invention is intended to be applicable to all variety of immunotherapies, including immunotherapies directed against foreign pathogens (e.g., viral, bacterial, fungal, or protozoan pathogens) and immunotherapies directed against malignancies. Thus, in some variations, the mammalian subject for immunotherapy is a subject having a cancer such as a cancer that expresses a least one tumor antigen (tumor associated antigen). Preferably, a subject having cancer comprises a cancer which expresses the same antigen that is comprised in the viral vector used for immunotherapy. In some cases a subject comprising a cancer may be a subject with a renal cell or a colorectal cancer. Preferably a mammalian subject is a human subject.

In addition to the immunotherapy methods described herein subjects may further be treated with one or more additional therapies such as a therapy considered the standard of care for a particular disease such as cancer. For example, the additional therapy or standard of care therapy may be chemotherapy, radiation therapy, surgery, or cytokine therapy.

Generally, an immunotherapy for use herein will be formulated in a pharmaceutically acceptable carrier, and may additionally comprise preservatives, salts and/or adjuvants.

In addition to the foregoing, the invention includes, as an additional aspect, all embodiments of the invention narrower in scope in any way than the variations specifically mentioned above. For example, although aspects of the invention may have been described by reference to a genus or a range of values for brevity, it should be understood that each member of the genus and each value or sub-range within the range is intended as an aspect of the invention. Likewise, various aspects and features of the invention can be combined, creating additional aspects which are intended to be within the scope of the invention. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION

I. Tumor-Associated Antigens (TAAs)

Figure 1:
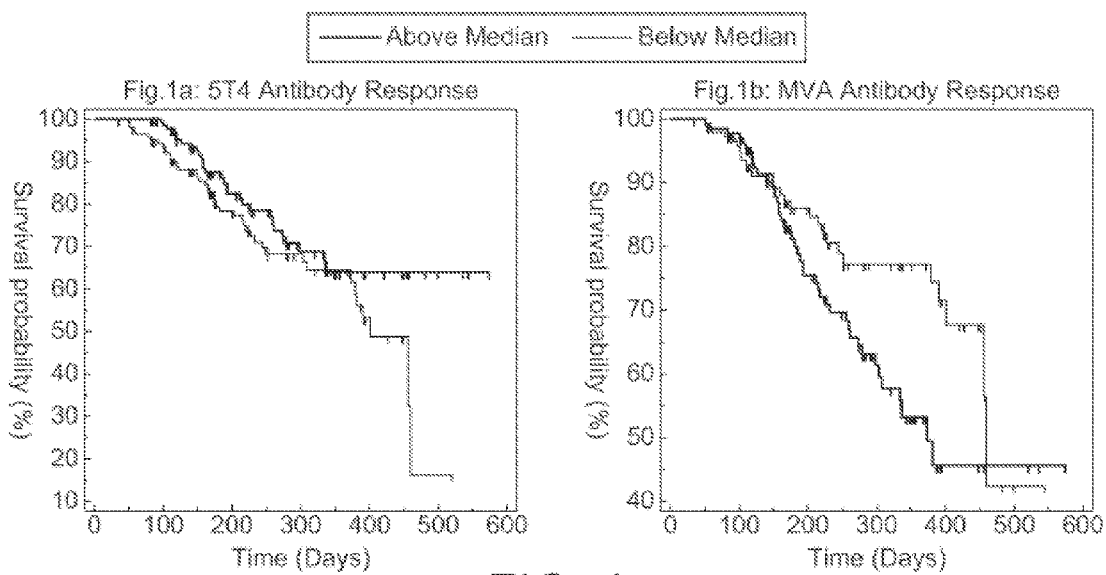
FIG. 1: Survival of TRIST patients stratified by above median vs below median 5T4 (FIG. 1a) or MVA (FIG. 1b) antibody responses at week 7.

In certain aspects the application concerns a tumor associated antigen. A suitable tumor associated antigen (TAA) or tumor antigens includes 5T4. As used herein the terms tumor associated antigen and tumor antigen are used interchangeably. Other suitable antigens include TAAs in the following classes: cancer testis antigens (e.g., HOM-MEL-40), differentiation antigens (e.g., HOM-MEL-55), overexpressed gene products (HOM-MD-21), mutated gene products (NY-COL-2), splice variants (HOM-MD-397), gene amplification products (HOM-NSCLC-11) and cancer related autoantigens (HOM-MEL-2.4) as reviewed in Cancer Vaccines and Immunotherapy (2000) Eds Stern, Beverley and Carroll, Cambridge University Press, Cambridge. Further examples include, MART-1 (Melanoma Antigen Recognized by T-cells-1) MAGE-A (MAGE-A1, MAGE-A2, MAGE-A3, MAGE-A4, MAGE-A6, MAGE-A8, MAGE-A10, MAGE-A12), MAGE B (MAGE-B1-MAGE-B24), MAGE-C (MAGE-C1/CT7, CT10), GAGE (GAGE-1, GAGE-8, PAGE-1, PAGE-4, XAGE-1, XAGE-3), LAGE (LAGE-1a (1S), -1b(1L), NY-ESO-1), SSX (SSX1-SSX-5), BAGE, SCP-1, PRAME (MAPE), SART-1, SART-3, CTp11, TSP50, CT9/BRDT, gp100, MART-1, TRP-1, TRP-2, MELAN-A/MART-1, Carcinoembryonic antigen (CEA), prostate-specific antigen (PSA), MUCIN (MUC-1) and Tyrosinase. TAAs are reviewed in Cancer Immunology (2001) Kluwer Academic Publishers, The Netherlands. Additional tumor associated antigens include Her 2, survivin and TERT.

The term "antigen" refers to protein or peptide to be introduced into a subject. As described herein, an antigen may be provided through delivering a peptide or protein or through delivering a nucleic acid encoding a peptide or protein.

By "antigen" in the context of the present invention it is also meant to incorporate an antigenic peptide derived from an antigen. In particular, "tumor associated antigen" is intended to encompass a peptide derived from a tumor associated antigen.

An antigen such as a tumor associated antigen can be provided for use as a medicament in a number of different ways. It can be administered as part of a viral vector. A number of suitable viral vectors will be familiar to those skilled in the art and include a number of vectors described herein.

II. TroVax® Vaccine

TroVax® (Oxford BioMedica plc) consists of a highly attenuated strain of vaccinia virus (VV), termed Modified Vaccinia Ankara, (MVA), and contains the human TAA 5T4 glycoprotein gene under regulatory control of a modified promoter, mH5.

MVA was developed as a safe vaccine for smallpox and MVA was derived from the VV Ankara strain by passaging in primary chick embryo fibroblasts (CEF), after which it was found to be replication defective in all mammalian cell lines tested, except Baby Hamster Kidney cells (BHK-21). Molecular genetic analysis of MVA has revealed substantial differences from the replication competent vaccinia virus which indicate that reversion of attenuation is highly unlikely. MVA is non-pathogenic in mammals including suckling mice, rabbits and primates. Importantly, no complications were reported when MVA was administered to over 120,000 subjects, many of who were at risk from vaccine complications. Replication of competent strains of VV are handled in a Biosafety level II environment; however, MVA has been assigned Biosafety level I status by the National Institutes of Health Intramural Biosafety Committee in the US, the UK Health and Safety Executive and the biosafety authorities in Germany.

5T4 is a 72 kDa oncofoetal glycoprotein that is expressed on over 70% of carcinomas of the kidney, breast, gastrointestinal tract, colon and ovaries. Unlike other self antigen TAAs such as CEA, 5T4 expression as detected by histochemical staining appears to be tumor specific with only low level sporadic staining observed in the gut and pituitary. However this level of staining is so low that it is difficult to determine if it is specific. Immunohistochemical analysis indicates that 5T4 expression is an indicator of poor prognosis in colorectal cancer. Additionally, when tumor cells are transduced with the cDNA encoding 5T4, they display increased motility suggesting that expression of this molecule may induce metastatic properties in a tumor.

TroVax® is able to induce an anti-5T4 antibody response in mice. Additionally, such a response is able to prevent the establishment of syngeneic tumor cells expressing human 5T4 in two murine tumor models. To model more accurately the possible anti-tumor effects of TroVax® in humans, MVA recombinants were constructed expressing the murine homologue of 5T4 (m5T4). In this self-antigen model MVA-m5T4 induction of an m5T4 antibody response was observed. Furthermore such a response is able to retard or prevent the establishment of syngeneic tumor cells expressing m5T4. Mice have been vaccinated on four occasions with MVA-m5T4 and there have been no reports of toxicity. In addition a number of studies have explored the toxicological consequences of immunization with TroVax®. Mice have been immunized with up to 12 repeated administrations of TroVax®. There were no TroVax® related deaths or adverse effects on clinical signs, body weight, food consumption, organ weights or clinical pathology. There were no macroscopic or microscopic findings suggestive of systemic toxicity due to the test articles.

Because 5T4 is an oncofoetal antigen, mice, previously vaccinated with MVA-m5T4, were used for breeding. It was found that immunity to m5T4 did not have a detrimental effect on the ability of mice to become pregnant or give birth to healthy progeny. In a more detailed study, female mice were administered with approx 107 pfu of TroVax® or MVA-m5T4 or placebo at 21 and 14 days prior to pairing with untreated males and, for the pregnant females, on day 6 of gestation. The pregnant females were maintained to day 18 of gestation then the injected animals and their respective foetuses analyzed macroscopically at necropsy. All clinical observations and necropsy findings were unremarkable. The pregnancy rate was slightly lower in the groups given both TroVax® and MVA-m5T4 compared to control. The toxicological significance of this finding is uncertain but may reflect a treatment impact on mating behavior. There was no adverse effect of treatment with either TroVax® or MVA-m5T4 on the uterine/implantation or foetal data. In summary, there was no female or maternal toxicity and no embryo-foetal toxicity in either group. Histological examination of the tissues from the MVA-m5T4 animals revealed no adverse microscopic findings.

It is apparent from pre-clinical studies that TroVax® has little potential to induce toxicity but is likely to induce an efficacious immune response to 5T4. In vivo studies suggest that such an immune response will have anti-tumor activity.

TroVax® has been administered to over 100 patients with metastatic colorectal or renal cancer. Over 450 doses have been administered. No serious adverse event attributed to TroVax® by investigators or the sponsor has been reported. Mild transient injection site reactions are reported in the majority of patients together with mild transient pyrexia. No other notable, common or serious adverse events have been reported in studies using TroVax® as a single agent in heavily pretreated patients or in studies combining TroVax® with chemotherapy, (5FU and leucovorin combined with either oxaliplatin or irinotecan), interferon-α, IL-2 (high dose intravenous regimen or low dose subcutaneous injections) or with sunitinib.

TroVax® induced an immune response against the 5T4 antigen in >90% of patients treated in all studies. An antibody or cellular immune response was observed in virtually all patients after the second or third injection of TroVax® and $CD8^+$ cellular responses were often higher than noted with other cancer vaccines reported in the literature. Of three Phase I or II studies conducted in colorectal cancer two demonstrated a correlation between tumor response and the anti-5T4 immune response. Notably this correlation was specific to the 5T4 immune response and there was no correlation with other markers of general immunocompetence. Objective responses have been noted in patients with metastatic renal cancer treated with TroVax® in combination with low dose IL-2. (Phase II studies with IFNα and sunitinib are ongoing and interim reports will be available for review by Investigators, IRB/Ethics Committees and Regulatory Authorities prior to commencement of this protocol).

III. Immunotherapy

In certain preferred aspects of the invention immunotherapic compositions and methods are used in cancer therapies. For example, immunotherapies maybe used to treat subjects having cancers including, but not limited to, non-solid tumors such as leukemia, multiple myeloma or lymphoma or solid tumors such as bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, placental, uterine and vulval tumors. In some further aspects a subject may be has a 5T4 or Carcinoembryonic antigen (CEA)-expressing cancer. In certain preferred aspects, a subject for treatment by the disclosed methods has a renal or colorectal cancer that will respond to treatment with immunotherapeutic agents, such as TroVax® as hereinbefore defined.

IV. Samples

In certain aspects, the disclosed methods concern collecting or obtaining a sample from a patient. As used herein, the term "sample" is intended to mean any biological fluid, cell, tissue, organ or portion thereof. The term includes samples obtained or derived from a subject. For example, a sample can be a histological section of a specimen obtained by biopsy, or samples that are placed in or adapted to tissue culture. Furthermore a sample can be a subcellular fraction or extract, or a crude or substantially pure protein preparation.

In the methods of the invention, a sample can be, for example, a cell or tissue obtained using a biopsy procedure or can be a fluid sample containing cells, such as blood, serum, semen, urine, or stool. Those skilled in the art will be able to determine an appropriate sample, which will depend on cancer type, and an appropriate method for obtaining a biopsy sample, if necessary. When possible, it can be preferable to obtain a sample from a patient using the least invasive collection means. For example, obtaining a fluid sample from a patient, such as blood, saliva, serum, semen, urine or stool, is less invasive than collecting a tissue sample.

EXAMPLES

Example 1

Study Details

The study was termed TRIST: TroVax® Renal Immunotherapy Survival Trial. An international Phase III, randomized, double blind, placebo controlled, parallel group study to investigate whether TroVax® added to first-line standard of care therapy, prolongs the survival of patients with locally advanced or metastatic renal clear cell adenocarcinoma.

The primary purpose of this trial is to demonstrate the effect of TroVax on survival in patients with locally advanced or metastatic renal clear cell adenocarcinomas. Clear cell adenocarcinomas of the kidney uniformly express 5T4 at high concentrations (80-90% of tumors examined) and are therefore an obvious candidate for treatment with a 5T4 vaccine.

Reported median survival times for this indication vary between studies but are generally in the range of 6 to 18 months depending on patient's status at entry and to a lesser extent on treatment. Novel forms of treatment are urgently needed.

This study will assess the impact on survival of adding TroVax® to the first-line standard of care for renal cancer. The current standard of care varies between countries and institutions and is influenced by the patient's status, the national regulatory status of different treatments and local reimbursement considerations. Commonly accepted standards of care for renal cancer include IL-2, IFNα, or a receptor tyrosine kinase inhibitor such as sunitinib. The use and availability of these treatments varies geographically.

High dose IL-2, although approved for the treatment of renal cancer is not included in this study as the high incidence of serious adverse events and need for intensive care limit its application and would complicate the safety evaluation of TroVax®.

The rationale for the potential concurrent use of IL-2 is that this compound is believed to act as an adjuvant. IL-2 is currently one of the standards of care regimens for the first line treatment of advanced and metastatic renal cancer. The dose schedule of IL-2 chosen is well recognized by the oncology community and has been validated in large scale Phase III clinical trials. Over 30 patients treated with a combination of TroVax® and IL-2 (high dose intravenous or low dose subcutaneous regimens) have been assessed in Phase II studies in patients with renal cancer. The combination was well tolerated. Compared with the historical adverse event profile of IL-2 alone the only additional adverse events reported were minor local reactions at the site of TroVax® injection and mild transient pyrexia. Humoral and/or cellular immune responses to 5T4 were induced in almost all patients and objective responses by RECIST have been reported.

Although it is not clear whether the biologic effects of IFNα occur entirely or in part via immunostimulation, there is evidence to show that it does have a modest clinical effect in renal cancer patients with an objective response rate of approximately 7.5-15%. Studies to determine whether IFNα increases survival in patients with renal cancer have produced inconsistent results. Given the immunological mechanism of action of IFNα, it is reasonable to evaluate the effect of TroVax® on survival in patients receiving this common standard of care. An ongoing study has not indicated any untoward safety impact resulting from co-administration of IFNα and TroVax®.

Phase II studies including over 20 patients treated with a combination of TroVax® and IFNα (three times weekly subcutaneous regimen) are ongoing in patients with renal cancer. Developing data indicate the combination to be well tolerated. Compared with the historical adverse event profile of IFNα alone the only additional adverse events reported are minor local reactions at the site of TroVax® injection and mild transient pyrexia. The expected humoral and/or cellular immune responses to 5T4 will be confirmed. Interim study reports will be available for review by regulatory authorities, IRB/Ethics Committees and investigators as part of the approval process of this study.

Recently developed oral kinase inhibitors, such as sorafenib and sunitinib, are becoming increasingly important in the management of advanced or metastatic renal cell carcinoma. Safety and immunology data necessary to support coadministration of sorafenib and TroVax® are not available. In view of this and the higher overall response rate reported with sunitinib the latter will be included in this study as an example of a kinase inhibitor used in the treatment of renal cancer.

Therefore, in regions where this treatment is approved, sunitinib may be used as the standard of care alongside TroVax®/placebo in this study. A Phase II study of patients treated with a combination of TroVax® and sunitinib (50 mg oral dose taken once daily, on a schedule of 4 weeks on treatment followed by 2 weeks off) is ongoing in patients with renal cancer. Developing data indicate the combination to be well tolerated. Compared with the reported data on sunitinib alone the only additional adverse events reported are minor local reactions at the site of TroVax® injection and mild transient pyrexia. The expected humoral and/or cellular immune response to 5T4 are to be confirmed. An interim study report will be available for review by regulatory authorities, IRB/Ethics Committees and investigators as part of the approval process of this study.

A cancer vaccine is intended to prolong survival by inducing an immune response to a tumor associated antigen. Preclinical models indicate that cancer vaccines may delay tumor growth and reduce the number of new metastases. It is not yet known whether a cancer vaccine must produce a high objective tumor response rate (by RECIST) in order to have clinically useful effect on prolonging survival. This will only be determined by a randomized survival study in patients receiving adequate vaccination to reliably induce an efficacious immune response. To date, both disease stabilization and late tumor responses have been reported with various cancer vaccines.

The maximum immunological response to TroVax® does not usually occur until the patient has received a minimum of three injections and it is not yet established whether continuing TroVax® despite early progression will confer therapeutic benefit. Therefore, in this study, if tumor progression is observed but the patient is tolerating TroVax®/placebo and their performance status remains at a Karnofsky score >60%, they should be requested to continue on study receiving TroVax®/placebo until they have received a minimum of eight injections of the study preparation. Continuation on study beyond this point to receive all TroVax®/placebo injections is permitted for such patients but is at the discretion of the investigator or patient.

A randomized, parallel group, double blind design is standard in Phase III efficacy studies. Interim statistical analyses conducted by an independent Data Safety Monitoring Board according to a pre-specified charter will be based on these interim analyses of safety and efficacy. The DSMB may recommend continuation of the study, stopping the study or stopping enrolment of patients of a specific treatment cell. The DSMB will also assess whether the frequency of events in the control arm matches the predictions used to determine the sample size of the study and may recommend changes to the number of events (deaths) triggering the final analysis.

TroVax® is a vaccine against a tumor-associated antigen. The assessment of such tumor vaccines for patients with solid tumors is complicated by a number of factors which influence the definition of the objectives, the route to achieving the objectives and the ongoing management of patients in the study.

Special features of tumor vaccines that are relevant to the objectives are listed below:

Vaccine-mediated immunotherapy requires repeated administration and time for the patient to develop an immune response to the vaccine antigen. In previous phase II studies it was shown that at least three administrations of TroVax® were required to generate a significant immune response. This means that patients who are removed from the study medication before receiving three injections of TroVax® due to death or rapidly progressive renal cancer, do not allow assessment of the potential of a TroVax®-induced immune response to provide benefit to patients treated for a longer period.

Cancer vaccines such as TroVax® may exert beneficial effects in delaying tumor growth and metastasis that do not manifest as RECIST responses but may prolong survival. This has implications for the management of patients because patients with a RECIST classification of progressive disease may still benefit from continuing with TroVax®.

It is not yet known whether tumor shrinkage predicts survival advantage. This means that the definitive efficacy endpoint is survival.

Objectives

Primary Efficacy Objective

To assess whether the addition of TroVax® to first line standard of care, will prolong survival of patients with locally advanced or metastatic clear cell renal adenocarcinoma when compared to placebo.

Analysis will occur after a predetermined number of deaths have occurred necessary to trigger the primary endpoint analysis or when specified by an independent Data Safety Monitoring Board based on analyses of interim data.

The analysis will be based on the Intent to Treat (ITT) population, composed of all patients.

Primary Safety Objective

To assess whether the addition of TroVax® to first line standard of care alters the profile of serious and non-serious adverse events, when compared to placebo, in patients with locally advanced or metastatic clear cell renal adenocarcinoma. This will be assessed in the Intent to Treat (ITT) population.

Secondary Efficacy Objectives

To compare the proportion of patients with progression free survival at 26 weeks (+/−1 week) in the TroVax® versus placebo arms based on radiological data. Data will be analyzed using the ITT population and adjudicated (blinded peer review) baseline and week 26 radiological data.

To compare the tumor response rates, time to response and duration of response between patients treated with TroVax® versus placebo. This will be analyzed in the Intent to Treat (ITT) population.

To assess whether the addition of a minimum of three doses of TroVax® to first line standard of care, will prolong survival of patients with locally advanced or metastatic clear cell renal adenocarcinoma when compared to placebo. This will be an exploratory analysis in the Modified Intent to Treat (MITT) population.

To assess whether TroVax® has an impact on the quality of life as measured by QLQ30 and EuroQOL questionnaires when compared to placebo. This will be analyzed in the Intent to Treat (ITT) population.

Endpoints

Primary Efficacy Endpoint

The survival event rate ratio in the TroVax® arm versus the placebo in the Intent to Treat (ITT) population based on the log of the hazard ratio derived from the Cox Proportional Hazards regression model. A frequentist monitoring approach will be used for evaluating the event ratio.

The key objective of this study is to determine whether TroVax® is able to prolong survival in patients receiving first line standard of care.

Analysis is triggered by a predetermined number of deaths in the study population or when specified by an independent Data Safety Monitoring Board based on analyses of interim data.

Primary Safety Endpoints

The number of adverse events (serious and non-serious) in the Intent to Treat population in the TroVax® versus the placebo arm.

The laboratory variables (complete blood count and chemistry panel) in the Intent to Treat (ITT) population in the TroVax® versus the placebo arm.

Secondary Efficacy Endpoints

The proportion of patients in the TroVax® versus placebo arms in the Intent to Treat (ITT) population with progression free survival at 26 weeks based on a comparison of baseline and week 26 (+/−1 week) radiological data and using RECIST criteria. Data will be adjudicated (blinded peer review).

Tumor response rates according to the investigator's reported interpretation of the radiological reports based on RECIST criteria observed in the Intent to Treat (ITT) population.

The survival event rate ratio in the TroVax® arm versus the placebo in the Modified Intent to Treat (MITT) population based on the log of the hazard ratio derived from the Cox Proportional Hazards regression model. A frequentist monitoring approach will be used for evaluating the event ratio.

The quality of life score for TroVax® versus placebo as measured by QLQ30 and EuroQOL questionnaires in the Intent to Treat (ITT) and Per Protocol populations.

Immunology Endpoint

Anti-5T4 antibody levels (additional measures of immune response including specific measures of cellular response will be investigated at some centres. Each will be the subject of a separate related protocol and informed consent for specific study sites and will be conditional upon regulatory and IRB/ethics committee approval before implementation.)

Metastatic renal cancer has a poor prognosis. The median survival overall has been reported to be as low as 6 months and five year survival is <5%. Conventional systemic cytotoxic chemotherapeutic agents and hormonal therapies have little impact on survival and response rates are usually <10%. The wide variations in the natural history of the disease and spontaneous regression rates of up to 6% have led to the investigation of immune mechanisms as a factor influencing responses and outcomes. Biological and immunologic therapies have demonstrated the best response rates with some impact on overall survival. However the management of metastatic renal cancer remains a therapeutic challenge.

Interferon alpha (IFNα) has demonstrated response rates of 8-26% with median survivals of 13 months. Interleukin-2 (IL-2) induces responses in 7-23% of patients with a median survival of 12 months. The benefit of biologic agents has been confirmed by randomized controlled trials, which have shown modest survival benefits with IFNα compared with medroxprogesterone or vinblastine. Motzer, in a retrospective analysis of 670 patients in 24 trials of systemic chemotherapy or cytokine therapies, demonstrated longer survival times with cytokine therapy. In the group who were long term survivors, 70% were in trials that involved IFNα and/or IL-2 and 30% had been treated with hormonal or cytotoxic agents.

The initial studies with IL-2 used protocols based on the principles of chemotherapy, using maximum tolerated doses. This was associated with significant renal, cardiac, pulmonary and haemodynamic toxicity, often requiring admission to intensive care wards and limiting utility to a selected subsection of the patient group. Subsequent studies of IL-2 have demonstrated similar efficacy, but with significantly less toxicity, using lower doses administered subcutaneously on an outpatient basis. In a study, comparing high and low-dose IL-2, there was a higher response rate with high dose treatment but this did not translate into survival benefit.

Negrier et al. assessed the use of these biologic agents as single agent therapy or combination therapy. They demonstrated response rates of 6.5%, 7.5% and 18.6% for IFNα, IL-2 or the combination, respectively. Although there was a difference in progression free survival, this did not translate into a survival advantage. The rationale for the combination of these agents is that, in vitro, IFNα enhances cell membrane expression of major histocompatibility antigens to which IL-2 activated T-cells can respond.

There is well-documented evidence to suggest that selection and prognostic factors significantly influence outcomes and responses to cytokine therapies. Motzer has assessed the prognostic value of a number of variables in patients with advanced or metatstic renal cell carcinoma. In these patients, low Karnofsky performance status, low haemoglobin level and high corrected serum calcium level indicated a poor prognosis. The median time to death in patients with zero risk factors was 22 months. The median survival in patients with one of these risk factors was 11.9 months and patients with 2-3 risk factors had a median survival of 5.4 months.

Two new drugs have recently been developed for the management of renal cancer: sunitinib and sorafenib. Both function by inhibiting multiple receptor kinases. Overall (complete and partial) response rates reported with sunitinib are substantially higher (25.5-36.5%) than reported with sorafenib (2%) though information on time to tumor progression and survival is still maturing.

Safety and immunology data necessary to support coadministration of sorafenib and TroVax® are not available. In view of this and the higher overall response rate reported with sunitinib the latter will be included in this study as an example of a receptor tyrosine kinase inhibitor used in the treatment of renal cancer.

Sunitinib malate is a small molecule that inhibits multiple receptor tyrosine kinase (RTKs), some of which are implicated in tumor growth, pathologic angiogenesis, and metastatic progression of cancer. Sunitinib was evaluated for its inhibitory activity against a variety of kinases (>80 kinases) and was identified as an inhibitor of platelet-derived growth factor receptors (PDGFRα and PDGFRβ), vascular endothelial growth factor receptors (VEGFR1, VEGFR2 and VEGFR3), stem cell factor receptor (KIT), Fms-like tyrosine kinase-3 (FLT3), colony stimulating factor receptor Type 1 (CSF-1R), and the glial cell-line derived neurotrophic factor receptor (RET). Sunitinib inhibition of the activity of these receptor tyrosine kinase (RTKs) has been demonstrated in biochemical and cellular assays, and inhibition of function has been demonstrated in cell proliferation assays. The primary metabolite exhibits similar potency to sunitinib when compared in biochemical and cellular assays.

The use of single agent sunitinib in the treatment of cytokine-refractory MRCC was investigated in two single-arm, multi-centre studies. All patients enrolled into these studies experienced failure of prior cytokine-based therapy. The primary endpoint for both studies was overall response rate (ORR). Duration of response (DR) was also evaluated.

One hundred and six patients were enrolled into Study 1, and 63 patients were enrolled into Study 2. Across the two studies, 95% of the pooled population of patients had at least some component of clear-cell histology. Patients received 50 mg sunitinib in cycles with 4 weeks on and 2 weeks off. Therapy was continued until the patients met withdrawal criteria or had progressive disease. There were 27 PRs in Study 1 as assessed by a core radiology laboratory for an ORR of 25.5% (95% CI 17.5, 34.9). There were 23 PRs in Study 2 as assessed by the investigators for an ORR of 36.5% (95% CI 24.7-49.6). The majority (>90%) of objective disease responses were observed during the first four cycles; the latest reported response was observed in cycle 10. DR data from Study 1 is premature as only 4 of 27 patients (15%) responding to treatment had experienced disease progression. At the time of the data cut-off, Study 1 was ongoing with 44 of 106 patients (41.5%) continuing treatment, and 11 of the 63 patients (17.5%) enrolled on Study 2 continued to receive sunitinib on continuation protocols.

As of March 2006 no data are available to determine whether sunitinib (or sorafenib) prolongs survival in patients with renal cancer.

Despite recent development of the kinase inhibitors, stage IV renal cell carcinoma is an area of high unmet medical need. The use of vaccines in this area is novel but capitalizes on the accepted opinion that immunologic mechanisms may have a part to play in the treatment of this disease.

Primary Efficacy Objective

To assess whether the addition of TroVax® to first line standard of care, will prolong survival of patients with locally advanced or metastatic clear cell renal adenocarcinoma when compared to placebo. This will be assessed in the Intent to Treat (ITT) population.

Primary Safety Objective

To assess whether the addition of TroVax® to first line standard of care alters the profile of serious and non-serious adverse events, when compared to placebo, in patients with locally advanced or metastatic clear cell renal adenocarcinoma. This will be assessed in the Intent to Treat (ITT) population.

Secondary Efficacy Objectives

To compare the proportion of patients with progression free survival at 26 weeks in the TroVax® versus placebo arms. This will be assessed in the Intent to Treat,(ITT) population.

To compare the tumor response rates, time to response and duration of response between patients treated with TroVax® versus placebo. This will be analysed in the Intent to Treat (ITT) population.

To assess whether the addition of a minimum of three doses of TroVax® to first line standard of care will prolong survival of patients with locally advanced or metastatic clear cell renal adenocarcinoma when compared to placebo. This will be an exploratory analysis in the Modified Intent to Treat (MITT) population.

To assess whether TroVax® has an impact on the quality of life as measured by QLQ30 and EuroQOL questionnaires when compared to placebo. This will be analyzed in the Intent to Treat (ITT) population.

Study Endpoints

Primary Efficacy Endpoint

The survival event rate ratio in the TroVax® arm versus the placebo in the Intent to Treat (ITT) population based on the log of the hazard ratio derived from the Cox Proportional Hazards regression model. A frequentist monitoring approach will be used for evaluating the event ratio.

Primary Safety Endpoints

The number of adverse events (serious and non-serious) in the Intent to

Treat population in the TroVax® versus the placebo arm.

The laboratory variables (complete blood count and chemistry panel) in the Intent to Treat (ITT) population in the TroVax® versus the placebo arm.

Secondary Efficacy Endpoints

The proportion of patients in the TroVax® versus placebo arms in the Intent to Treat (ITT) population with progression free survival at 26 weeks based on a comparison of baseline and week 26 (+/−1 week) radiological data and using RECIST criteria. Data will be adjudicated (blinded peer review).

Tumor response rates according to the investigator's reported interpretation of the radiological reports based on RECIST criteria observed in the Intent to Treat (ITT) population.

The survival event rate ratio in the TroVax® arm versus the placebo in the Modified Intent to Treat (MITT) population based on the log of the hazard ratio derived from the Cox Proportional Hazards regression model. A frequentist monitoring approach will be used for evaluating the event ratio.

The Quality of Life score for TroVax® versus placebo as measured by QLQ30 and EuroQOL questionnaires in the Intent to Treat (ITT) and Per Protocol populations.

Immunology Endpoint

Anti-5T4 antibody levels (additional measures of immune response including specific measures of cellular response will be investigated at some centers. Each will be the subject of a separate related protocol and informed consent for specific study sites and will be conditional upon regulatory and IRB/ethics committee approval before implementation.)

Study Population

Patients of any ethnic group with histologically proven clear cell renal adenocarcinoma who have had their primary tumor surgically removed and require treatment for locally advanced or metastatic disease. The intent is to include 700 patients split equally between the TroVax® and placebo arms.

Study Design

This is an international, randomized, double blind, placebo controlled, parallel group study to investigate whether a minimum of three doses of TroVax® added to first-line standard of care therapy, prolongs the survival of patients with locally advanced or metastatic renal clear cell adenocarcinoma.

The primary endpoint is survival. The study is designed to be pragmatic, limiting additional study related investigations to a minimum. Protocol mandated scans and X-rays are limited to two time points (baseline and week 26) to permit comparison of the percentage of patients with progressive disease at 6 months as a secondary efficacy endpoint. Six months was selected based on review of published literature indicating that progressive disease was commonly observed by 26 weeks in patients with renal cancer. Endpoints such as tumor response by RECIST are considered of secondary importance to survival and will be determined by radiological examinations ordered at the discretion of the investigator based on the clinical status of the patient and will be based the interpretation of the patient's care-team (investigator and local radiologist).

Study enrolment will only commence at each centre once ethics and regulatory approval have been obtained from the relevant authorities.

After signing the study informed consent form and meeting the baseline enrolment criteria patients will be assigned by the investigator (their physician) to one of the following defined first-line standard of care regimens based on what is best for the patient and consistent with local practice:

1. subcutaneous low dose IL-2
2. interferon alpha (excluding pegylated IFNalpha)
3. sunitinib Only after the standard of care therapy has been decided should the investigator telephone the Interactive Voice Recognition Service (IVRS). Randomization to TroVax® or placebo will be stratified based on the standard of care chosen by the investigator, study prognostic indicators (Motzer score) and geography.

TroVax® is administered at a dose of $1 \times 10^9$ TCID50/ml in 1 ml by injection into the deltoid muscle of the upper arm at regular intervals up to 8 weeks apart up to a maximum of 13 doses.

An independent Data Safety Monitoring Board will be responsible for preparing the formal monitoring rules for this study. This parallel-designed study contains a series of planned interim assessments for futility, and to ensure that the planning elements relative to attrition and the primary endpoint remain consistent. A frequentist monitoring approach will be used for evaluating the event rate ratio to ensure that the assumptions are accurate and the sample size continues to be appropriate for assessing superiority. The DSMB may recommend changes to the enrollment target if pretrial assumptions prove inaccurate. These DSMB reviews will be conducted confidentially. Data analysis will not be shared with the sponsor, investigators or any other participant in the study.

Study Design

Type of Study

This is an international, randomised, double blind, placebo controlled, parallel group study designed to assess whether, when added to first-line standard of care, TroVax® prolongs survival in patients with locally advanced or metastatic renal carcinoma.

The primary endpoint is survival. The study is designed to be pragmatic, limiting additional study related investigations to a minimum. Protocol mandated scans and X-rays are limited to two time points (baseline and week 26) to permit comparison of the percentage of patients with progressive disease at 6 months as a secondary efficacy endpoint. Six months was selected based on review of published literature indicating that progressive disease was commonly observed by 26 weeks in patients with renal cancer. Endpoints such as tumor response by RECIST are considered of secondary importance to survival and will be determined by radiological examinations ordered at the discretion of the investigator based on the clinical status of the patient and will be based the interpretation of the patient's care-team (investigator and local radiologist).

Study enrolment of 700 patients will only commence once ethics and regulatory approval has been obtained from the relevant authorities.

After signing the study informed consent form and meeting the baseline enrolment criteria patients will be assigned by the investigator (their physician) to one of the following defined standard of care regimens based on what is best for the patient and consistent with local practice:

1. subcutaneous low dose IL-2
2. interferon-α (excluding pegylated IFNα)
3. sunitinib Only after the standard of care therapy has been decided should the investigator telephone the Interactive Voice Randomization Service (IVRS). Randomisation to TroVax® or placebo will be stratified based on the standard of care chosen by the investigator, the study site and prognostic indicators.

An independent Data Safety Monitoring Board will periodically review emerging data. These reviews will be conducted confidentially. Data analysis will not be shared with the sponsor, investigators or any other participant in the study. A frequentist monitoring approach will be used for evaluating the event rate ratio to ensure that the assumptions are accurate and the sample size continues to be appropriate for assessing superiority. The DSMB may recommend changes to the enrollment target if pretrial assumptions prove inaccurate.

Rationale for Study Design

A randomized, parallel group, double blind design is standard in Phase III efficacy studies. Interim statistical analyses conducted by an independent Data Safety Monitoring Board will ensure that the trial can be closed if shown to be futile or resized if it turns out that the assumptions made about the primary endpoint in the control group are inaccurate.

Study Sites, Duration and Recruitment Rates

This is an international trial with recruitment across approximately 100 sites. The recruitment rates are estimated to be approximately 0.5 to 4 patients per site per month. Since this is a survival study patients are expected to be on study for a median time of 12 months.

Justification of the Proposed Dosing Regimen

In the TroVax® Phase I study four dose levels were studied ($1 \times 10^8$ TCID50/ml, $2 \times 10^8$ TCID50/ml, $5 \times 10^8$ TCID50/ml, and $1 \times 10^9$ TCID50/ml) and two different routes of administration, intramuscular and intradermal, were compared. There was no clinically or statistically significant difference in peak immune response though the highest dose produced a slightly earlier antibody response. No difference was observed between the routes of administration in terms of antibody response. All doses and routes were well tolerated with only local injection site reactions which were of similar frequency. In view of a trend to an earlier antibody response the dose of $1 \times 10^9$ TCID50/ml was selected.

In subsequent Phase II studies involving >70 patients, a dose level of $1 \times 10^9$ TCID50/ml was used and safety, tolerability and immunogenicity were confirmed.

In this study, TroVax®/placebo is administered at weeks 1, 3, 6, 9, 13, 17, 21, 25, 33, 41, 49, 57 and 65. This frequency is influenced by experience gained in phase II studies in patients with renal or colorectal cancer where TroVax® was co-administered with either combination chemotherapy, IL-2 or IFNα.

Study Population

Patient Recruitment

A total of 700 patients with clear cell renal carcinoma will be enrolled in the study. Eligible patients will have had the primary tumor surgically removed.

Patients will receive one of the following defined standards of care:

subcutaneous low dose IL-2 interferon alpha (excluding pegylated IFNα)

sunitinib

The choice of first-line standard of care for each patient will be made by the patient's physician based on normal clinical criteria, local standard of care, and local regulatory and reimbursement status or economic availability. Once treatment is selected, patients will be randomized to TroVax® or placebo.

Patients will be recruited internationally. Patients of all ethnic groups are eligible for the study.

Entry Criteria

Patients who meet the following inclusion criteria and none of the exclusion criteria will be included in this study.

Inclusion Criteria

Signed informed consent. The patient must be competent to give written informed consent and comply with the protocol requirements.

Locally advanced or metastatic, histologically proven clear cell renal carcinoma.

Primary tumor surgically removed (some residual advanced primary tumor may remain).

At least four weeks post surgery or radiotherapy (defined from time of randomisation.)

First-line. No prior therapy for renal cancer except surgery or radiotherapy.

Measurable disease.

Aged 18 years or more.

Patient expected to survive a minimum of 12 weeks (i.e. in the opinion of the investigator there is a >90% probability that the patient will survive >12 weeks if treated with the selected standard of care).

Free of clinically apparent autoimmune disease (including no prior confirmed diagnosis or treatment for autoimmune disease including Systemic Lupus Erythematosis, Grave's disease, Hashimoto's thyroiditis, multiple sclerosis, insulin dependant diabetes mellitus or systemic (non-joint) manifestations of rheumatoid disease).

Total white cell count ≥3×109/L and lymphocyte count ≥1×109/L.

Serum creatinine ≤1.5 times the upper limit of normal.

Bilirubin ≤2 times the upper limit of normal and an SGPT of ≤4 times the upper limit of normal.

Women must be either post menopausal, or rendered surgically sterile or, if of child bearing potential, must have been practicing a reliable form of contraception (oral contraception+a barrier method) for at least three months prior to the first dose of TroVax® and must continue while they are being treated with TroVax®. Men must practice a reliable form of contraception (barrier or vasectomy) while they are being treated with TroVax®.

No acute changes on 12-lead ECG.

Ejection fraction documented as not less than 45% or no clinical suspicion that cardiac ejection fraction is less than 45% (If clinical suspicion exists the ejection fraction should be measured according to local site procedures).

Karnofsky performance status of ≥80%.

Exclusion Criteria

Cerebral metastases. (Known from previous investigations or clinically detectable).

Previous exposure to TroVax®.

Serious infections within the 28 days prior to entry to the trial.

Known to test positive for HIV or hepatitis B or C.

Life threatening illness unrelated to cancer.

History of allergic response to previous vaccinia vaccinations.

Known allergy to egg proteins.

Known hypersensitivity to neomycin.

Participation in any other clinical trial of a licensed or unlicensed drug within the previous 30 days or during the course of this trial.

Previous malignancies within the last 10 years other than successfully treated squamous carcinoma of the skin or in situ carcinoma of the cervix treated with cone biopsy.

Previous history of major psychiatric disorder requiring hospitalization or any current psychiatric disorder that would impede the patient's ability to provide informed consent or to comply with the protocol.

Oral corticosteroid use unless prescribed as replacement therapy in the case of adrenal insufficiency.

Ongoing use of agents listed in locally approved prescribing information as causing immunosuppression.

Prior history of organ transplantation.

Pregnancy or lactation.

Withdrawal Criteria

In accordance with applicable regulations, a patient has the right to withdraw from the study at any time and for any reason without prejudice to his or her future medical care by the physician or at the institution.

If a patient is withdrawn from treatment with TroVax®/placebo because of an adverse event (AE), the event will be followed up until it has resolved or has stabilized. Because this is a survival study patients should continue to be followed until death to document subsequent treatment and survival status In addition to AEs, other reasons for removal of patients from the study would be the patient's withdrawal of consent. Should this happen, since this is a survival study, the patient's physician must request consent from the patient for survival follow up.

Withdrawal from the study, and reason for withdrawal, must be documented in the CRF.

Because the primary endpoint of this study is survival and all randomised patients will be included in the primary or secondary endpoint analysis. Patients who wish to withdraw from all other study related procedures for any reason should be asked whether they would consent to follow up limited to documenting their subsequent management and survival status. If they agree, a new informed consent form should be used to document consent to such follow up.

Treatment Plan and Methods

| | | Study Schedule: | | | | | | | | | |
|---|---|---|---|---|---|---|---|---|---|---|---|
| | | Base line | Wk 1 | Wk 2 | Wk 3 | Wk 4 | Wk 5 | Wk 6 | Wk 7 | Wk 8 | Wk 9 | Wk 10 |
| TroVax®/Placebo day 1/wk Patients only | | | X | | X | | | X | | | X | |
| receive one of these treatments | | Patients receive only one of the following treatments | | | | | | | | | | |
| | IL-2 Treatment days 1-5 each wk | | X | X | X | X | X | X | | | Continue with 6 weeks subcutaneous IL-2 followed by 2 weeks without IL-2 every 8 weeks until tumor progression or week 46 (whichever is first) | |
| | | OR | | | | | | | | | | |
| | IFNα | Subcutaneous IFNα day 1, 3 and 5 of each week until tumor progression (refer to nationally approved prescribing information or institutional guidelines of use of IFNα for renal cancer). | | | | | | | | | | |
| | | OR | | | | | | | | | | |
| | sunitinib | | X | X | X | X | | | | | Continue with 4 weeks on sunitinib then 2 weeks without sunitinib every 6 weeks until tumor progression. (see nationally approved sunitinib prescribing information) | |
| | | Patients receive all the following procedures | | | | | | | | | | |
| Consent form | | X | | | | | | | | | | |
| Randomisation | | | X | | | | | | | | | |
| Medical History | | X | | | | | | | | | | |
| Physical examination | | X | | | | | X | | | | | |
| Blood for Immuno (10 ml) | | X | | | | | | X | | | | X |
| Weight, BP, Pulse, Temp | | X | X | | X | | | X | | | X | |
| CBC/Diff/Plts | | X | X | | X | | | X | | | X | |

Study Schedule:

| | | | | | | |
|---|---|---|---|---|---|---|
| Chemistry Panel | X* | X | X | X | X | |
| CT or MRI Chest, Abd, Pelvis | X | | | | | |
| 12 lead ECG | X | | | | | |
| Echocardiogram+ | X | | | | | |
| Karnofsky | X | | X | X | X | |
| Tumor histopathology | X | | | | | |
| Pregnancy Test (if applicable) | X | colspan: Prior to TroVax ®/placebo if any possibility of pregnancy | | | | |
| QOL | X | | | X | X | |
| Concomitant Therapy | colspan: Record on each visit that patient receives TroVax ®/placebo | | | | | |
| AEs | colspan: Throughout the study while patient receiving TroVax ®/placebo and 30 days after | | | | | |
| Subsequent renal cancer Rx | colspan: Record other renal cancer treatment once patient is not receiving TroVax ®/placebo | | | | | |
| Survival status/date of death | colspan: Record on each visit that patient receives TroVax ®/placebo and every 12 weeks thereafter. If patient does not return to clinic seek survival status and date of death as permitted by patient consent | | | | | |

| | | Wk 11 | Wk 12 | Wk 13 | Wk 14 | Wk 15 | Wk 16 | Wk 17 | Wk 18 |
|---|---|---|---|---|---|---|---|---|---|
| TroVax ®/Placebo day 1/wk Patients only | | | | X | | | | X | |
| | | colspan: Patients receive only one of the following treatments | | | | | | | |
| receive one of these treatments | IL-2 Treatment days 1-5 each wk | colspan: Continue with 6 weeks subcutaneous IL-2 followed by 2 weeks without IL-2 every 8 weeks until tumor progression or week 46 (whichever is first) OR | | | | | | | |
| | IFNα | colspan: Subcutaneous IFNα day 1, 3 and 5 of each week until tumor progression (refer to nationally approved prescribing information or institutional guidelines of use of IFNα for renal cancer). OR | | | | | | | |
| | sunitinib | colspan: Continue with 4 weeks on sunitinib then 2 weeks without sunitinib every 6 weeks until tumor progression. (see nationally approved sunitinib prescribing information) | | | | | | | |
| | | colspan: Patients receive all the following procedures | | | | | | | |
| Consent form | | | | | | | | | |
| Randomisation | | | | | | | | | |
| Medical History | | | | | | | | | |
| Physical examination | | | | X | | | | | |
| Blood for Immuno (10 ml) | | | | | | | | | |
| Weight, BP, Pulse, Temp | | | | X | | | | X | |
| CBC/Diff/Plts | | | | X | | | | X | |
| Chemistry Panel | | | | X | | | | X | |
| CT or MRI Chest, Abd, Pelvis | | | | | | | | | |
| 12 lead ECG | | | | | | | | | |
| Echocardiogram+ | | | | | | | | | |
| Karnofsky | | | | X | | | | X | |
| Tumor histopathology | | | | | | | | | |
| Pregnancy Test (if applicable) | | colspan: Prior to TroVax ®/placebo if any possibility of pregnancy | | | | | | | |
| QOL | | | | X | | | | X | |
| Concomitant Therapy | | colspan: Record on each visit that patient receives TroVax ®/placebo | | | | | | | |
| AEs | | colspan: Throughout the study while patient receiving TroVax ®/placebo and 30 days after | | | | | | | |
| Subsequent renal cancer Rx | | colspan: Record other renal cancer treatment once patient is not receiving TroVax ®/placebo | | | | | | | |
| Survival status/date of death | | colspan: Record on each visit that patient receives TroVax ®/placebo and every 12 weeks thereafter. If patient does not return to clinic seek survival status and date of death as permitted by patient consent | | | | | | | |

-continued

Study Schedule:

| | | Wk 19 | Wk 20 | Wk 21 | Wk 22 | Wk 23 | Wk 24 | Wk 25 | Wk 26 | Wk 27 | Wk 28 |
|---|---|---|---|---|---|---|---|---|---|---|---|
| TroVax ®/Placebo day 1 Patients only | | | | X | | | | | X | | |
| | | Patients receive only one of the following treatments | | | | | | | | | |
| receive one of these treatments | IL-2 Treatment days 1-5 each wk | Continue with 6 weeks sub-cutaneous IL-2 followed by 2 weeks without IL-2 every 8 weeks until tumor progression or week 46 (whichever is first) OR | | | | | | | | | |
| | IFNα | Subcutaneous IFNα day 1, 3 and 5 of each week until tumor progression (refer to nationally approved prescribing information or institutional guidelines of use of IFNα for renal cancer). OR | | | | | | | | | |
| | sunitinib | Continue with 4 weeks on sunitinib then 2 weeks without sunitinib every 6 weeks until tumor progression. (see nationally approved sunitinib prescribing information) | | | | | | | | | |
| | | Patients receive all the following procedures | | | | | | | | | |
| Physical examination | | | | | | | | X | | | |
| Weight, BP, Pulse, Temp | | | | X | | | | X | | | |
| CBC/Diff/Plts | | | | X | | | | X | | | |
| Chemistry Panel | | | | X | | | | X | | | |
| CT or MRI Chest Abd, Pelvis | | | | | | | | | X | | |
| Karnofsky | | | | X | | | | X | | | |
| QOL | | | | X | | | | X | | | |
| Pregnancy Test (if applicable) | | Prior to TroVax ®/placebo if any possibility of pregnancy | | | | | | | | | |
| Concomitant Therapy | | Record on each visit that patient receives TroVax ®/placebo | | | | | | | | | |
| AEs | | Throughout the study while patient receiving TroVax ®/placebo and 30 days after | | | | | | | | | |
| Subsequent renal cancer Rx | | Record other renal cancer treatment once patient is not receiving TroVax ®/placebo | | | | | | | | | |
| Survival status/date of death | | Record on each visit that patient receives TroVax ®/placebo and every 12 weeks thereafter. If patient does not return to clinic seek survival status and date of death as permitted by patient consent | | | | | | | | | |

| | | Wk 29 | Wk 30 | Wk 31 | Wk 32 | Wk 33 | Wk 34 | Wk 35 | Wk 36 | Wk 37 |
|---|---|---|---|---|---|---|---|---|---|---|
| TroVax ®/Placebo day 1 Patients only | | | | | | X | | | | |
| | | Patients receive only one of the following treatments | | | | | | | | |
| receive one of these treatments | IL-2 Treatment days 1-5 each wk | Continue with 6 weeks sub-cutaneous IL-2 followed by 2 weeks without IL-2 every 8 weeks until tumor progression or week 46 (whichever is first) OR | | | | | | | | |
| | IFNα | Subcutaneous IFNα day 1, 3 and 5 of each week until tumor progression (refer to nationally approved prescribing information or institutional guidelines of use of IFNα for renal cancer). OR | | | | | | | | |
| | sunitinib | Continue with 4 weeks on sunitinib then 2 weeks without sunitinib every 6 weeks until tumor progression. (see nationally approved sunitinib prescribing information) | | | | | | | | |
| | | Patients receive all the following procedures | | | | | | | | |
| Physical examination | | | | | | | X | | | |
| Weight, BP, Pulse, Temp | | X | | | | | X | | | |
| CBC/Diff/Plts | | X | | | | | X | | | |
| Chemistry Panel | | X | | | | | X | | | |
| CT or MRI Chest Abd, Pelvis | | | | | | | | | | |
| Karnofsky | | X | | | | | X | | | |
| QOL | | X | | | | | X | | | |
| Pregnancy Test (if applicable) | | Prior to TroVax ®/placebo if any possibility of pregnancy | | | | | | | | |
| Concomitant Therapy | | Record on each visit that patient receives TroVax ®/placebo | | | | | | | | |
| AEs | | Throughout the study while patient receiving TroVax ®/placebo and 30 days after | | | | | | | | |
| Subsequent renal cancer Rx | | Record other renal cancer treatment once patient is not receiving TroVax ®/placebo | | | | | | | | |

Study Schedule:

| | |
|---|---|
| Survival status/date of death | Record on each visit that patient receives TroVax ®/placebo and every 12 weeks thereafter. If patient does not return to clinic seek survival status and date of death as permitted by patient consent |

| | | Wk 38 | Wk 39 | Wk 40 | Wk 41 | Wk 42 | Wk 43 | Wk 44 | Wk 45 | Wk 46 | Wk 47 |
|---|---|---|---|---|---|---|---|---|---|---|---|
| TroVax ®/Placebo day 1 Patients only | | | | | X | | | | | | |
| | | | | | Patients receive only one of the following treatments | | | | | | |
| receive one of these treatments | IL-2 Treatment days 1-5 each wk | | | Continue with 6 weeks subcutaneous IL-2 followed by 2 weeks without IL-2 every 8 weeks until tumor progression or week 46 (whichever is first) | | | | | | No further IL-2 | |
| | | | | OR | | | | | | | |
| | IFNα | | | Subcutaneous IFNα day 1, 3 and 5 of each week until tumor progression (refer to nationally approved prescribing information or institutional guidelines of use of IFNα for renal cancer). | | | | | | | |
| | | | | OR | | | | | | | |
| | sunitinib | | | Continue with 4 weeks on sunitinib then 2 weeks without sunitinib every 6 weeks until tumor progression. (see nationally approved sunitinib prescribing information) | | | | | | | |
| | | | | Patients receive all the following procedures | | | | | | | |
| Physical examination | | | | | X | | | | | | |
| Weight, BP, Pulse, Temp | | | | | X | | | | | | |
| CBC/Diff/Plts | | | | | X | | | | | | |
| Chemistry Panel | | | | | X | | | | | | |
| Karnofsky | | | | | X | | | | | | |
| QOL | | | | | X | | | | | | |
| Pregnancy Test (if applicable) | | | | Prior to TroVax ®/placebo if any possibility of pregnancy | | | | | | | |
| Concomitant Therapy | | | | Record on each visit that patient receives TroVax ®/placebo | | | | | | | |
| AEs | | | | Throughout the study while patient receiving TroVax ®/placebo and 30 days after | | | | | | | |
| Subsequent renal cancer Rx | | | | Record other renal cancer treatment once patient is not receiving TroVax ®/placebo | | | | | | | |
| Survival status/date of death | | | | Record on each visit that patient receives TroVax ®/placebo and every 12 weeks thereafter. If patient does not return to clinic seek survival status and date of death as permitted by patient consent | | | | | | | |

| | | Wk 48 | Wk 49 | Wk 50 | Wk 51 | Wk 52 | Wk 53 | Wk 54 | Wk 55 | Wk 56 |
|---|---|---|---|---|---|---|---|---|---|---|
| TroVax ®/Placebo day 1 Patients only | | | X | | | | | | | |
| | | Patients receive only one of the following treatments | | | | | | | | |
| receive one of these treatments | IL-2 Treatment days 1-5 each wk | | | No further IL-2 | | | | | | |
| | | | | OR | | | | | | |
| | IFNα | | | Subcutaneous IFNα day 1, 3 and 5 of each week until tumor progression (refer to nationally approved prescribing information or institutional guidelines of use of IFNα for renal cancer). | | | | | | |
| | | | | OR | | | | | | |
| | sunitinib | | | Continue with 4 weeks on sunitinib then 2 weeks without sunitinib every 6 weeks until tumor progression. (see nationally approved sunitinib prescribing information) | | | | | | |
| | | | | Patients receive all the following procedures | | | | | | |
| Physical examination | | | | X | | | | | | |
| Weight, BP, Pulse, Temp | | | | X | | | | | | |
| CBC/Diff/Plts | | | | X | | | | | | |
| Chemistry Panel | | | | X | | | | | | |
| Karnofsky | | | | X | | | | | | |
| QOL | | | | X | | | | | | |
| Pregnancy Test (if applicable) | | | Prior to TroVax ®/placebo if any possibility of pregnancy | | | | | | | |
| Concomitant Therapy | | | Record on each visit that patient receives TroVax ®/placebo | | | | | | | |
| AEs | | | Throughout the study while patient receiving TroVax ®/placebo and 30 days after | | | | | | | |
| Subsequent renal cancer Rx | | | Record other renal cancer treatment once patient is not receiving TroVax ®/placebo | | | | | | | |
| Survival status/date of death | | | Record on each visit that patient receives TroVax ®/placebo and every 12 weeks thereafter. If patient does not return to clinic seek survival status and date of death as permitted by patient consent | | | | | | | |

-continued

Study Schedule:

| | | Wk 57 | Wk 58 | Wk 59 | Wk 60 | Wk 61 | Wk 62 | Wk 63 | Wk 64 | Wk 65 | Wk 66 | Subsequent weeks |
|---|---|---|---|---|---|---|---|---|---|---|---|---|
| TroVax ®/Placebo day 1 Patients only | | X | | | | | | | | X | | |
| | | | colspan Patients receive only one of the following treatments | | | | | | | | | |
| receive one of these treatments | IL-2 Treatment days 1-5 each wk | | | | | No further IL2 | | | | | | |
| | | | | | | OR | | | | | | |
| | IFNα | | | | | Subcutaneous IFNα day 1, 3 and 5 of each week until tumor progression (refer to nationally approved prescribing information or institutional guidelines of use of IFNα for renal cancer). | | | | | | |
| | | | | | | OR | | | | | | |
| | sunitinib | | | | | Continue with 4 weeks on sunitinib then 2 weeks without sunitinib every 6 weeks until tumor progression. (see nationally approved sunitinib prescribing information) | | | | | | |
| | | | | | | Patients receive all the following procedures | | | | | | |
| Physical examination | | X | | | | | | | | X | | Continue follow-up for survival |
| Weight, BP, Pulse, Temp | | X | | | | | | | | X | | Record subsequent therapy for renal cancer |
| CBC/Diff/Plts | | X | | | | | | | | X | | |
| Chemistry Panel | | X | | | | | | | | X | | |
| Karnofsky | | X | | | | | | | | X | | |
| QOL | | X | | | | | | | | X | | |
| Pregnancy Test (if applicable) | | | | | | Prior to TroVax ®/placebo if any possibility of pregnancy | | | | | | |
| Concomitant therapy | | | | | | Record on each visit that patient receives TroVax ®/placebo | | | | | | |
| AEs | | | | | | Throughout the study while patient receiving TroVax ®/placebo and 30 days after | | | | | | |
| Subsequent renal cancer Rx | | | | | | Record other renal cancer treatment once patient is not receiving TroVax ®/placebo | | | | | | |
| Survival status/date of death | | | | | | Record on each visit that patient receives TroVax ®/placebo and every 12 weeks thereafter. If patient does not return to clinic seek survival status and date of death as permitted by patient consent | | | | | | |

If clinically indicated * including LDH at baseline
Timing of all TroVax ® injections +/−3 days. Timing of all laboratory and clinical observations must remain the same relative to TroVax ®. Week 26 scan may vary by +/−7 days.

Allocation of Treatments and Randomization Procedures

Treatment (TroVax® or placebo) will be allocated based on stratified randomization. The primary objective of stratification will be to ensure that the distribution of first-line standard of care treatment is balanced between the two study arms. Secondary objectives of stratification will be to establish balance between the treatment arms with regard to a prognostic index (Motzer score) and geography.

Motzer et al demonstrated in a series of 670 patients with advanced renal cell carcinoma that survival correlated with five prognostic factors: Karnofsky performance status (<80%), high lactate dehydrogenase (LDH) level (>1.5 times the upper limit of normal), low haemoglobin level (less than the lower limit of the gender normal), high corrected serum calcium level (>10 mg/dL), and absence of nephrectomy. The higher the number of positive factors the worse the prognosis. Inclusion criteria for this study require a baseline Karnofsky performance status ≥80% and prior excision of the primary tumor. During the randomization procedure the patient's haemoglobin level (plus gender), LDH and serum calcium will be requested to ensure that the treatment arms are balanced with regard to these prognostic variables.

A telephone based interactive voice responsive system will be used. Patients will be registered into the study using an Interactive Voice Responsive System (IVRS). Treatment allocation (TroVax® or placebo) and patient registration will only occur after the Investigator has registered the standard of care therapy allocated to the patients and confirmed that the patient meets all inclusion/exclusion criteria. All randomized patients will be included in Intent to Treat (ITT) analyses.

Instruction on access and use of the IVRS service including local telephone access number, script of the randomization questions in local language and help desk numbers will be issued separate from the protocol.

Study Medication Administration

Patients included in this trial should receive TroVax® or placebo plus one of the following first-line standards of care treatment options: IL-2 (low dose), interferon a or sunitinib. No other form of immunotherapy, chemotherapy, or radiotherapy should be administered between entering the study and tumor progression. Other concurrent medication may be used as detailed in "Other Concurrent Treatments" below. Following tumor progression patients may receive whatever chemotherapy, radiotherapy, cytokine therapy or other therapy is indicated for further management or palliation of the tumor. All such therapy should be recorded on the patient's case report form as the patient continues to be followed for survival.

Administration of TroVax®/Placebo

Prior to administering the vaccine, obtain the prospective patient's vaccination history and determine whether the individual had any previous reactions to any vaccine including TroVax®.

All immunizations of TroVax®/placebo will be given by intramuscular injection into the deltoid muscle of the upper arm.

All patients will receive the treatment in a side-room away from contact with other patients. The formulation will be delivered to this side-room. TroVax®/Placebo are presented as lyophilised material. Detailed instructions will be provided to the pharmacist for reconstitution. TroVax® must be resuspended by adding 1.2 mL of water for injection. The resulting solution will appear opalescent. One mL volume of the solution is then withdrawn into a syringe and injected into the patient. The injection will either be drawn up at the bedside by the person administering the dose, or in the pharmacy and delivered to the bedside in a syringe depending upon local circumstances. Prior to injection the check number of the dose must be confirmed, using IVRS, by either the pharmacist or another responsible individual.

UNDER NO CIRCUMSTANCES MUST THE RECONSTITUTED MATERIAL BE ALLOWED TO STAND FOR MORE THAN TWO HOURS AT ROOM TEMPERATURE. IF THIS DOES OCCUR, THE MATERIAL MUST BE REJECTED AND IVRS NOTIFIED.

The skin will be swabbed with ethanol and the injection will be given intramuscularly. Following this, the injection site will be covered with an occlusive bandage. This bandage will be removed before the patient is discharged from hospital.

Please note: The maximum immunological response to TroVax® does not usually occur until the patient has received at least three injections. Disease stabilisation or late tumor responses have been reported with various cancer vaccines. It is not established whether continuing TroVax® despite early progression will confer therapeutic benefit. If tumor progression is observed but the patient is tolerating TroVax®/placebo and their performance status remains at a Karnofsky score >60% they should be requested to continue receiving TroVax®/placebo until they have received a minimum of eight injections. Continuation beyond this point is permitted at the discretion of the investigator and patient.

Patients should remain under medical observation for one hour following injection with TroVax®/placebo.

Adequate treatment provisions, including epinephrine injection (1:1000), should be available for immediate use should an anaphylactic reaction occur.

All healthcare staff handling TroVax® or materials contaminated by it must wear an apron, gloves, mask, and protective goggles. All materials potentially contaminated with TroVax® e.g. syringes, swabs, bandages, must be destroyed by incineration, or local equivalent, in accordance with hospital policy on genetically modified materials. Certificates of Destruction, or equivalent, must be completed for the used and unused vials, and copies maintained in the Trial File.

Administration of IL-2

IL-2 (Chiron or locally approved manufacturer) will be given by subcutaneous injection. The lyophilised material (22 million units) must be reconstituted in 1.2 mL of diluent after which it will have a shelf life of 48 hours when kept refrigerated at 2-8° C. The dosage schedule will be an initial dose of 250,000 U/Kg/dose (with an upper limit of 22 million units/dose) for 5 days out of 7 in week 1 of each cycle followed by 125,000 U/kg/dose (with an upper limit of 11 million units/dose) for 5 days in each of weeks 2-6 of each cycle. There will then be a two week recovery period before the next cycle of IL-2 commences. Once reconstituted a vial may be used for two injections when these are given on consecutive days.

The dose used should be recorded in the Case Report Form.

Administration of IFNα

IFNα will be administered once a day as a subcutaneous injection three times per week on days 1, 3 and 5 of each week. (Note: Pegylated IFNα is not included as a standard of care option in this protocol. No safety or immunological activity data are currently available on the concomitant use of TroVax® and pegylated IFNα).

Unless tumor progression is noted the patient should be treated for a minimum of 12 weeks. Treatment may be continued until tumor progression at the discretion of the investigator.

Doses of IFNα used by different treatment centers depend on local Regulatory Authority approved label text, and manufacturer. The dose used in this study should reflect local standard of care but should be targeted between 9 million International Units (IU) and 18 million IU three times per week. Lower doses should be used during the first (and depending on final target dose) the second week. The actual schedule used will be recorded on the Case Report Form.

For further information on IFNα please refer to the nationally approved Package Insert or Summary of Product Characteristics produced by the local license holder.

For evaluation of patients for clinical benefit from the treatment please see study schedule. Patients who are benefiting from treatment are eligible for further treatment. Thereafter, therapy will continue until criteria for progressive disease are met or up to an additional 12 months.

Administration of Sunitinib

Sunitinib capsules are supplied as printed hard shell capsules containing sunitinib malate equivalent to 12.5 mg, 25 mg or 50 mg of sunitinib and should be handled according to the manufacturers instructions. The recommended dose of sunitinib for advanced Renal Cell Cancer is one 50 mg oral dose taken once daily, on a schedule of 4 weeks on treatment followed by 2 weeks off. Sunitinib may be taken with or without food.

The schedule used should be recorded in the Case Report Form.

Treatment should continue until tumor progression or until unacceptable toxicity occurs.

Administration of Other Concurrent Treatments

All other concurrent medications will be recorded in detail in the CRF during the treatment. This information may be used to assist interpretation of any report adverse events. If a patient has discontinued TroVax®/placebo and other renal cancer treatments are used, then a simple checklist in the CRF will be used to record the type of treatment; this information may be used to assist interpretation of survival data and management of the patient following the selected standard of care therapy.

Medication intended to relieve symptoms will be prescribed at the discretion of the Investigator and recorded in the Case Report Form (CRF). Medications prescribed by the patient's family practitioner will also be noted in the CRF. The patients should also keep a record of any over the counter medicines consumed and these should be noted in the CRF.

Therapies considered necessary for the subject's well being may be administered at the discretion of the investigator. These will be recorded in the Case Report Form.

Supportive care to mitigate known adverse events or complications of concomitant standard of care may be administered at the physician's discretion including antipyretics, non-steroidal anti-inflammatories, anti-emetics, etc. Oral, intramuscular or intravenous steroids should not be used except where required to manage life threatening emergencies. Supportive care will be reported in the Case Report Form.

Management of Disease Progression

If disease progression is noted during the study, and other anticancer medications are required, the IL-2, IFNα, or sunitinib should be stopped. The selection of subsequent antitumor therapy is not specified by this protocol and is at the discretion of the patient and his or her physician.

In the event of tumor progression the patients should remain within the study (unless they request to withdraw). This is for two reasons:

This is a survival study and patients need to be followed for survival data.

The maximum immunological response to TroVax® does not usually occur until the patient has received at least three injections. Disease stabilization or late tumor responses have been reported with various cancer vaccines. It is not established whether continuing TroVax® despite early progression will confer therapeutic benefit. Therefore if tumor progression is observed but the patient is tolerating TroVax®/placebo and their performance status remains at a Karnofsky score >60% they should be requested to continue receiving TroVax®/placebo until they have received a minimum of eight injections of the study preparation. Continuation on study beyond this point to receive all TroVax®/placebo injections is permitted at the discretion of the investigator or patient.

Specific Procedures

Screening and Selection Procedures

A screening log must be maintained for all patients screened for entry to the study including, if applicable, the reason for not entering the study.

Inclusion/exclusion criteria are listed in the section titled Entry Criteria (above) and the study schedule.

Imaging/Diagnostic

Within 2 weeks of screening, and prior to receiving study drug metastases will be documented using chest, abdominal and pelvic CT scans according to defined guidelines contained in a Site Operations Manual. This will enable a possible independent review at a later time. An MRI or CT scan of the brain will also be obtained if there is a clinical suspicion of cerebral metastases.

Clinical and Laboratory/Diagnostic

For screening, these are required within 14 days before the first TroVax®/Placebo injection:

History and physical examination, including height, weight, and vital signs.

Karnofsky performance status.

Quality of life (QLQ30,EuroQOL) will be evaluated.

12 lead EGC (for all patients) and Echocardiogram only if clinically indicated

Clinical pathology tests (Full blood count with differential white cell and platelet counts, urea and electrolytes, liver function tests (total bilirubin, AST, ALT, alkaline phosphatase), serum proteins, calcium, phosphate, uric acid and creatinine) In addition, at baseline LDH must be measured.

Pregnancy test (for women of reproductive potential— including those whose last menstrual period was within the last two years). At screening this will be a serum test but at all other timepoints this will be a urine test.

If available, tumor tissue from earlier biopsies will be obtained. (To be batched and tested at a later date for the presence of tumor antigens.)

All clinical laboratory tests will be conducted by a suitably qualified central laboratory.

Samples for Immunology 10 mL blood samples will be required. These samples are to be placed in a heparinized blood collection tube and are to be processed immediately by a suitably qualified central laboratory. The samples will then be analyzed by Oxford BioMedica, or designee, according to their SOPs.

Study Materials

TroVax®/Placebo

TroVax®/Placebo will be supplied by Oxford BioMedica (UK) Ltd.

Packaging and labeling and additional information

Packaging and labeling will be in accordance with Good Manufacturing Practice (GMP) for clinical trials.

Each vial will bear a label conforming to national regulations for an Investigational Medicinal Product.

The outer carton labeling will also bear a label conforming to national regulations for an Investigational Medicinal Product.

Investigators and pharmacists should note that the clinical trial supplies may only be used for the clinical trial for which they are indicated. They must not be employed for any other trial, whether of TroVax® or not, or for any other clinical use.

Additional information may be found in the current version of the Investigators Brochure.

Storage and Disposition of Study Medications

TroVax®/placebo must be stored in a locked fridge between 2° C. to 8° C. (36° F. to 46° F.) in the hospital pharmacy, or other comparable secure location. It must be stored in such a way that it cannot be mixed up or confused with other medications, be they clinical trial supplies or medicines for routine clinical use.

Dispensing will be documented by completing a log with the date of dispensing and the patient details. Used vials should be stored in labeled biohazard bags or containers prior to reconciliation by the trial monitor.

At each visit, the clinical trial monitor will review the drug-dispensing log and reconcile it with the unused vials (if available due to local procedures). All unused vials will be destroyed on site in accordance with procedures for destruction of genetically modified waste and destruction will be documented appropriately. A copy of the Certificate of Destruction will be lodged in the site Trial File.

Precautions/Overdose

TroVax® is contraindicated in patients who have previously had hypersensitive reactions to TroVax®, vaccinia vaccinations, egg proteins or neomycin.

Patients should remain under medical observation for one hour following injection with TroVax.

Adequate treatment provisions, including epinephrine injection (1:1000), should be available for immediate use should an anaphylactic reaction occur.

TroVax® is also contraindicated in patients who are pregnant or lactating.

Although highly unlikely, it is possible that an autoimmune response against the pituitary or gut might occur since these organs showed sporadic low level staining for 5T4 in in vitro experiments. Studies in over 100 patients receiving approximately 450 doses of TroVax® have not indicated any laboratory or clinical signs or symptoms suggestive of compromised pituitary function. However, the Investigators should be aware of the preclinical finding.

All healthcare staff handling TroVax® or materials contaminated by it must wear an apron, gloves, a mask and protective goggles. Pregnant healthcare staff must not handle either TroVax® or materials contaminated with TroVax®.

No cases of TroVax® overdose have been reported. No active medical intervention is known to be required in the event of overdose. The patient should be observed for as long as is considered appropriate by the investigator/physician based on the patient's clinical condition and supportive care given if required.

IL-2

IL-2 is available commercially from Chiron or a local manufacturer. The lyophilized material (22 million units) must be reconstituted in 1.2 mL of diluent after which it will have a shelf life of 48 hours when kept refrigerated.

Current prescribing information should be reviewed prior to administering IL-2.

IFNα

IFNα is available commercially from a number of manufactures. Only commercially available material approved by the competent national regulatory authority should be used in this study IFNα may be supplied in single use prefilled syringes or in multiuse prefilled "pens". Patients will be instructed to self administer the IFNα in accord with approved package insert and patient information leaflet by appropriately qualified medical, nursing or pharmacy staff. Reconstitution is not required.

IFNα should be stored at 2° to 8° C. (36° F. to 46° F.).

Current prescribing information should be reviewed prior to administering IFNα.

Sunitinib

Sunitinib is supplied as 12.5 mg, 25 mg and 50 mg capsules which should be administered according to the manufacturer's instructions (Pfizer).

Other Study Supplies

Case report forms (CRFs) will be used in this study (see Data Collection section below). Quality of life questionnaires EuroQOL and QLQ30 and laboratory kits will also be supplied. The Principal Clinical Investigator and Co-Investigators must keep all CRF supplies, both completed and blank, in a secure place.

Adverse Events

Adverse Event Definition

An adverse event is any untoward medical occurrence in a patient or clinical investigation subject administered a pharmaceutical product and which does not necessarily have to have a causal relationship with the treatment. All adverse events must be described in the appropriate section of the CRF and their severity and putative relationship to the study medication noted. Definitions of severity are as follows:

Mild: does not interfere with the conduct of the study, resolves spontaneously, does not need medication or any other therapy.

Moderate: requires treatment, interferes temporarily with the conduct of the study.

Severe: forces withdrawal from the study

Serious: death, life threatening, requires or prolongs hospitalization, results in persistent or significant disability/incapacity, overdose, or is a congenital anomaly/birth defect Definitions of relationship to study medication are as follows:

Unrelated: bears no relation to timing of medication, similar to symptoms or signs expected in the disease process, does not recur on re-challenge.

Possibly: bears relation to timing of medication, similar to symptoms or signs expected in the disease process, does not recur on re-challenge.

Probably: bears clear relation to timing of medication, distinct from symptoms or signs expected in the disease process, does not recur on re-challenge.

Definitely: bears clear relation to timing of medication, distinct from symptoms or signs expected in the disease process, recurs on re-challenge.

Adverse events may also be expected or unexpected. Adverse events are to be considered expected if listed in the Investigator Brochure.

Serious Adverse Event (SAE) and Serious Adverse Reaction (SAR) Definition

Investigators are required to notify Oxford BioMedica's pharmacovigilance service provider (PAREXEL) immediately if a patient has a reportable serious adverse event. A serious adverse event (SAE) is defined by ICH-GCP as:

Death (death due to progressive renal cancer is the primary endpoint of this study and should not be reported as an adverse event unless in the opinion of the investigator the study medication (TroVax®/placebo) may possibly, probably or definitely have contributed to or hastened death)

Life threatening

Requires or prolongs hospitalization

Results in persistent or significant disability/incapacity

Congenital anomaly/birth defect

Other medically important condition starting or worsening during the study

The investigator must also complete as much as possible of the serious adverse event form in the Case Report Form (CRF) and transfer it to Oxford BioMedica's pharmacvigilance service provider (PAREXEL) not later than 24 hours after the even becomes known to the investigator or his/her staff The report must be made by fax to: +44 1895 231847

The Email contact is: drugsafety@parexel.com

Hotline number for 24 hours cover is: +44 1895 273 434

As further information or follow up information becomes available the investigator should document this and amend any previous report if appropriate. This information should be transferred to Oxford BioMedica's pharmacovigilance service provider (PAREXEL) using the serious adverse event form in the CRF.

PAREXEL will report all serious, related, and unexpected adverse events to all relevant Regulatory Authorities in accordance with local regulations.

Further instructions on the documentation and transfer of information to permit full compliance with national and international pharmacovigilance requirements and Good Clinical Practice together with training for investigator staff will be provided separate to this protocol.

General Requirements

This study will utilize the Common Terminology Criteria for Adverse Events Version 3 to determine the severity of the reaction for adverse event reporting.

Reporting requirements and procedures depend upon:
whether agents are suspected of causing the adverse event,
whether the possibility of such an adverse event was reported in the protocol, consent form, or manufacturer's literature (expected or unexpected adverse event),
the severity or grade of the adverse event.

Withdrawals Due to Adverse Events

If a patient is withdrawn from treatment because of an adverse event (AE), the patient will be followed up until the AE is resolved or has stabilized. Because the primary endpoint of this study is survival the patient will continue to be followed for survival status even if trial therapy was withdrawn.

Withdrawal from the study, and reason for withdrawal, must be documented in the CRF.

Since the primary endpoint of this study is survival and all randomised patients will be included in the analysis of the primary endpoint. Patients who wish to withdraw from all other study related procedures should be asked whether they would consent to allow follow up limited to establishing their survival status. If they agree, a new consent form to document this consent but withdrawal from all other study procedures should be completed.

Pregnancy

Patients should be advised that they or their partner should avoid becoming pregnant during the study.

Patients of reproductive potential should be taking contraceptive measures as required by the relevant inclusion criterion (as stated above).

If a patient does become pregnant she should immediately inform the investigator who should document this on the adverse events page of the CRF. The Investigator should provide necessary counseling for the patient. The Investigator should follow the pregnancy to its conclusion. Spontaneous abortion or foetal abnormality or abnormal birth should be reported as serious adverse events as described above.

Management of Toxicity

The NCI Common Terminology Criteria for Adverse Events v3.0 (CTCAE) will be utilized (see Appendix A). Toxicity will be evaluated on every patient visit.

All toxic events should be managed with optimal supportive care, including transfer to the Intensive Care Unit if appropriate.

TroVax®/Placebo Management of Toxicity

No dose reductions of TroVax®/placebo are permitted. Paracetamol/acetaminophen may be used to manage transient pyrexia or local discomfort following injection If the patient is unable to tolerate TroVax®/placebo at the protocol dose TroVax®/placebo should be discontinued but the patient should continue to be followed for survival data.

Standard of Care Management of Toxicity

Toxicity associated with standard of care therapy should be managed according the nationally approved Package Insert or Summary of Product Characteristics and accepted medical practice. Dosage may be reduced or withdrawn at the discretion of the Investigator.

Data Management and Statistical Analyses

Overview of the Study Design

The DSMB will be responsible for preparing the formal monitoring rules for this study; a general overview of the monitoring program is described in this section of the protocol. Oxford BioMedica will provide guidance to the DSMB, however the Board is an independent body and will be charged with preparing the formal monitoring and stopping rules for the study. This parallel-designed study contains a series of planned interim assessments for futility, and to ensure the planning elements relative to attrition and the primary endpoint remain consistent. The initial interim assessment will take place after 50 patients (25 patients per arm or ~7% of the target population) have been randomised and followed for 8 weeks when the blood sampling for 5T4 antibodies following the third dose of TroVax® is scheduled to be performed. The intra-treatment group adverse event profiles, rates of attrition, and antibody response will be evaluated by the DSMB. Sample size estimates for this study are predicated on a one year survival.

Sample Size Estimates

Estimates were prepared to detect an absolute difference of ~11% in survival at 1-year (base proportions: 50% to 61%); estimates are presented below in Table 1.0.

TABLE 1

| | | | Estimates Based on Overall Survival | | | | |
|---|---|---|---|---|---|---|---|
| Power | Total Sample Size (N) | Total Required Events | Alpha | Beta | Proportion Surv. (S1) | Proportion Surv. (S2) | Hazard Ratio |
| 0.80 | 691 | 309 | 0.05 | 0.2 | 0.500 | 0.605 | 0.725 |

A total sample size of ~700 patients (split equally between the two groups), or 309 events, achieves 80% power to detect a hazard rate of 0.725 when the proportions surviving in each group are 0.500 and 0.605 at a significance level of 0.05 using a two-sided test. These estimates represent the initial framework for monitoring based on the log of the hazard ratio from the Cox Proportional Hazards regression model without adjusting for covariates.

Report Definitions

Power is the probability of rejecting a false null hypothesis.

Events are the number of deaths (from whatever cause) that must occur in each group.

Alpha is the probability of rejecting a true null hypothesis.

Beta is the probability of accepting a false null hypothesis.

S1 is the proportion surviving in group 1, S2 is the proportion surviving in group 2.

HR is the hazard ratio. It is calculated using $\text{Log}(S2)/\text{Log}(S1)$.

This sample size would also be appropriate for detecting a minimum difference in median survival of ~11.3 weeks, based on exponential survival times (Table 2). Details used in preparing this estimate are presented below.

TABLE 2

| | | | Comparing Median Survival (H0: Theta1 = Theta2, Ha: Theta1 <> Theta2) | | | | | |
|---|---|---|---|---|---|---|---|---|
| Power | N1 | N2 | Allocation Ratio | Alpha | Beta | Theta1 | Theta2 | Theta1/ Theta2 |
| 0.80000 | 350 | 350 | 1.00000 | 0.05000 | 0.20000 | 48.0 | 59.3 | 0.80902 |

Report Definitions

Power is the probability of rejecting a false null hypothesis.

N1 is the number of failures needed in Group 1, N2 is the number of failures needed in Group 2.

Alpha is the probability of rejecting a true null hypothesis.

Beta is the probability of accepting a false null hypothesis.

Theta1 is the Mean Life in Group 1, Theta2 is the Mean Life in Group 2.

Patient Populations

The Intent to Treat (ITT) population will include all patients who are randomized.

The Modified Intent to Treat (MITT) population will include all patients who receive three or more injections, or experience an adverse event directly attributable to the study medication resulting in discontinuation, prior to the third injection. Patients who fail to successfully receive three injections for reasons not directly associated with the study medication will not be included in this population.

The Per Protocol (PP) population includes only patients who met the inclusion and exclusion criteria and were treated in accord with the protocol requirements.

The primary efficacy analysis will be carried out using the ITT population. However, an exploratory analysis of the primary efficacy parameter will also be carried out using MITT population and the PP population. All safety analyses will be carried out using the Intent to Treat population.

Monitoring of the Primary Endpoint

The DSMB may recommend stopping the trial early if presented with overwhelming evidence of efficacy.

Evidence would be deemed "overwhelming" if the one-sided P-value in favor of the active treatment derived from the Cox Proportional Hazards time-to-death model is less than 0.01%. The overall effect of treatment must also be considered clinically plausible by the DSMB.

P-values will be adjusted to maintain an overall one-sided P-value of 2.5% using the alpha-spending approach of Lan and Demets (Lan K K G and DeMets D L (1983) Discrete sequential boundaries for clinical trials. Biometrika 70: 659-663).

The DSMB will review at each meeting the number of patients lost to follow-up. If the number of patient lost to follow-up is high enough to compromise the objectives of the study the DSMB may either recommend terminating the study on the grounds that it will not effectively address its objective or alternatively resizing the study to permit the objective of the study to be appropriately address.

The DSMB may also recommend stopping the trial early if presented with evidence of futility. At each interim analysis the conditional power will be calculated. If, taking into account the whole clinical context, the DSMB considers the prospect of achieving a statistically significant result within a reasonable sample size to be unacceptably low, then the DSMB may recommend stopping the trial.

The methodology for study re-sizing will follow that of Li, Shih, Xie and Lu (Li G, Shih W J, Xie T and Lu J (2002) A sample size adjustment procedure for clinical trials based on conditional power. Biostatistics 3: 277-287).

Statistical Analyses

Unless otherwise stated, all statistical tests will be performed using 2-sided tests at the 5% significance level. Baseline is defined as the last observation before the initiation of the study related treatment. Continuous demographic parameters, such as the patient's age at the time of enrolment, will be summarised for the ITT population using descriptive statistics (N, mean, median, standard deviation, minimum and maximum value, and 95% 2-sided confidence limits) and compared between groups using a 2-sample t-test. Categorical parameters will be summarised as a proportion of the ITT population and compared using a 2-tailed Fisher's Exact test. Co-morbid risk factors will be summarised for the ITT population by treatment assignment and according to the type of variable (categorical, continuous) and compared between groups. Kaplan-Meier estimates for the time to death will be prepared based on the ITT population. Event rates at 12- and 24-months will be derived from the Kaplan-Meier estimates. The number and proportion of patients alive after each treatment cycle will be tabulated and summarized using 95% confidence intervals. Separate tables containing patient counts, percentages, and 95% binomial confidence intervals will be prepared based on risk factors. No data will be imputed for patients who withdrew prematurely from the study, or have missing values for specific parameters.

Univariate analyses will be prepared for each laboratory parameter and compared between groups using a 2-sample t-test. The proportion of patients found to have abnormal values considered clinically significant will be compared between treatment groups using a 2-tailed Fisher's Exact test. Laboratory shift tables containing patient counts and percentages will be prepared by treatment assignment, laboratory parameter, and time.

Demography

Patient demographic data will be summarised by type of variable; categorical data by counts and percentages and continuous variable by means, standard deviations, medians, minimum, maximum and numbers of patients.

Analysis of Efficacy Data

The standard covariates for the efficacy analyses are:

Geographical region (three groups: USA, European Union, Eastern Europe excluding European Union)

First line of standard care (three groups: IL-2, interferon-α, sunitinib)

Prognostic index (Motzer score). (Motzer score classifies patients into three prognostic groups: "favorable", "intermediate" and "poor" based on an algorithm which considers pre-treatment performance status, LDH, hemoglobin, and corrected serum calcium. The inclusion and exclusion criteria preclude enrolment of the "poor" prognostic group. All eligible patients will be covered in the remaining two groups)

Primary

The primary endpoint is time to death. Time to death will be analyzed in the ITT population using a Cox Proportional Hazards regression model with terms for treatment and the standard efficacy covariates.

Secondary

The secondary efficacy endpoints will be analysed following the statistical procedures presented below.

Endpoint: The proportion of patients with progression free survival at 26 weeks (+/−1 week) based on radiological data in the ITT population.

The proportion of patients with progression free survival at 26 weeks (+/−1 week) relative to baseline will be analyzed using a logistic regression model with terms for treatment and the standard efficacy covariates. Data will be analyzed using the ITT population and adjudicated (blinded peer review).

Endpoint: Tumor response rates based on RECIST according to the investigator's reported interpretation of the radiological reports observed in the ITT population.

Both the rate and duration of tumor response will be compared between treatment groups. Response rates will be compared between treatment groups and analyzed using a logistic regression model with terms for treatment and the standard efficacy covariates The duration of response will be analysed using a Cox Proportional Hazards regression model with terms for treatment and the standard efficacy covariates.

Endpoint: The survival event rate ratio in the TroVax® arm versus the placebo arm in the MITT population, based on the log of the hazard ratio.

Time to death will be analyzed using a Cox Proportional Hazards regression model with terms for treatment and the standard efficacy covariates. Survival curves for the proportion of patients remaining event-free will be estimated using the Kaplan-Meier method Endpoint: Anti-5T4 serum antibody levels (additional measures of immune response including specific measures of cellular response will be investigated at some centers).

Qualitative antibody response to 5T4 within the active treatment group will be analysed as a main effect using a logistic regression model with terms for the standard efficacy covariates.

The analysis of the Quality of Life parameters is discussed in Section 12.8.

Analysis of Adverse Event Data

Safety will be assessed using the Intent to Treat population. Adverse events will be coded using the MedDRA classification to give a preferred term and organ class for each event. Proportions of patients with adverse events will be presented. Tables of adverse events will be presented by organ class and also by organ class and preferred term. These tables will also include overall totals for adverse events within each body system and organ class. The number of patients with an event in each classification of severity and relationship to treatment within each treatment group will be tabulated. Serious adverse events and adverse events leading to withdrawal will be listed separately.

Treatment emergent and non-emergent events will be presented separately. Treatment emergent adverse events are defined as adverse events that had an onset day on or after the day of the first dose of study medication. Adverse events that have missing onset dates will be considered to be treatment emergent.

Adverse events will be listed by patient within groups showing time of onset, period of event, severity, relationship to disease and outcome.

QOL Parameters

Results from the QOL questionnaire (EuroQoL and QLQ30) will be presented for the ITT and Per-Protocol populations. Results from the QOL questionnaire will be analyzed using a generalized linear modeling approach based on maximum likelihood, treating patients as a random effect in the model. Terms will be included for the standard efficacy covariates.

Concomitant Medication

Concomitant medication will be listed by patient, treatment assignment, and study visit.

Vital Signs

Vital signs to be collected throughout the course of the study include systolic and diastolic blood pressures (mmHg), heart rate (bpm), body temperature (° C./° F.), and weight (kg). Vital signs will be summarised using univariate statistics (N, arithmetic average, standard deviation, median, and range) for each clinical assessment and presented for the cohort of patients who have data at the initial baseline visit and at least one the specific follow-up visits. In addition to the univariate statistics, the changes from baseline to each follow-up assessment visit will be analyzed using a paired-difference t-test for the within-group mean change from baseline. Additionally, 95% confidence interval limits for the mean change from baseline will also be reported.

The incidence rates of clinically notable vital sign changes, including the criteria for clinically notable, will be summarized and presented in a Patient Data Listing. Vital signs and body weight abnormalities of potential clinical significance will be defined as follows:

Systolic blood pressure change 20 mmHg and a systolic blood pressure value that was ≥180 or ≤90 mmHg Diastolic blood pressure change 15 mmHg and a diastolic blood pressure value that was ≥105 or ≤50 mmHg Pulse change of 15 bpm and a pulse value that was ≥120 or ≤50 bpm Temperature change of 1° C./2° F. and a temperature value that was 38° C./101° F.

Body weight decrease ≥5%

Clinically significant abnormal vital signs will be flagged and presented using counts by study visit.

An additional listing will be provided for those patients who have clinically significant vital sign abnormalities.

Other Safety Parameters

All other safety parameters will be listed by patient, treatment assignment, and study treatment period.

Laboratory Parameters

Haematology, biochemistry and other laboratory data will be listed at each time point by treatment group and, for appropriate values, will be flagged using the signed laboratory ranges as High/Low/Within laboratory normal range (H, L).

Changes from baseline will also be listed and abnormal changes from baseline will be flagged.

An additional listing will be provided for those patients who have laboratory values that are abnormal and considered to be clinically significant.

Withdrawals

The number (%) of patients who withdraw from the study over time, along with their reasons for withdrawal, will be tabulated.

Deaths

All deaths occurring during the treatment period of study and its follow up period will be listed.

Determination of Treatment Group Comparability

Patient demographics and disease histories will be summarized for each treatment group and compared between treatment groups.

Treatment Assignment

Patients will be randomised using a stratified central randomisation scheme. Given the initial target enrolment and the proposed number of clinical sites, attempting to balance the enrollment on an intra-center basis was not considered feasible using a deterministic randomization scheme. For example, if patients were to be randomized intra-center using randomized blocks of 4, and 50% of the sites failed to fill a complete block, an enrollment imbalance could develop between the 2 groups resulting in a loss of statistical power. To eliminate this potential imbalance, a central randomization scheme will be used, balancing on blocks of 4 within geographical areas (usually countries) involving multiple sites.

Stratification

Patients will be stratified by selected standard of care, prognostic indicator (Motzer score), geographical area, and institution. The stratification will be performed by IVRS.

Example 2

Analysis of Study Data

Background

Following the announced ending of the TRIST phase III clinical trial, immunological and clinical response data were un-blinded. An exploratory analysis was undertaken with the primary aim of identifying potential correlates between immunological response parameters and enhanced patient survival.

Methodology

TRIST is an international Phase III study investigating the potential survival benefit of adding a cancer vaccine, TroVax®, to standard of care treatments for patients with renal cell cancer. Immunological analyses have been conducted on patients as part of the TRIST clinical protocol comprising an analysis of antibody responses against the 5T4 tumor antigen and the MVA viral vector. These were quantified at 3 time points:

1. Baseline (pre-TroVax®/placebo vaccination).
2. Week 7 (following 3 TroVax®/placebo vaccinations)
3. Week 10 (following 4 TroVax®/placebo vaccinations)

The analyses summarized below have focused solely on the immune responses detected in patients known to have received TroVax®. The magnitude of the 5T4-specific or MVA-specific antibody response has been analyzed separately at week 7 and week 10 (post 3rd and 4th TroVax® vaccination respectively) and a median value calculated for the entire patient group (i.e. median 5T4 antibody response at week 7 for TroVax® treated patients, median MVA antibody response at week 7 for TroVax® treated patients etc). Each patient was then categorized into "above median" or "below median" category. The survival of patients in each antibody response category was compared by plotting Kaplan-Meier curves.

Results

Initially, antibody responses to 5T4 antigen or MVA (whole, irradiated MVA) were analyzed separately by ELISA. FIG. 1 illustrates "above median" and "below median" antibody response categories for 5T4 (FIG. 1a) and MVA (FIG. 1b) at week 7 in TroVax®-treated TRIST patients.

The data summarized in FIG. 1 suggest that patients with higher (above median) 5T4 antibody responses at week 7 survive for longer than those with below median 5T4 antibody levels. Conversely, patients with above median MVA antibody levels appear to fair worse than those with weaker (below median) MVA antibody responses.

Following this observation, a combination of 5T4 and MVA antibody responses was examined and categorized patients into 4 categories. Results are shown in Table 3.

TABLE 3

| Antibody Response Category | Nomenclature Used | | 5T4 Antibody Response | | MVA Antibody Response | |
|---|---|---|---|---|---|---|
| | 5T4 | MVA | Above Median | Below Median | Above Median | Below Median |
| 1 | Above | Above | ✓ | | ✓ | |
| 2 | Above | Below | ✓ | | | ✓ |
| 3 | Below | Above | | ✓ | ✓ | |
| 4 | Below | Below | | ✓ | | ✓ |

Figure 2:
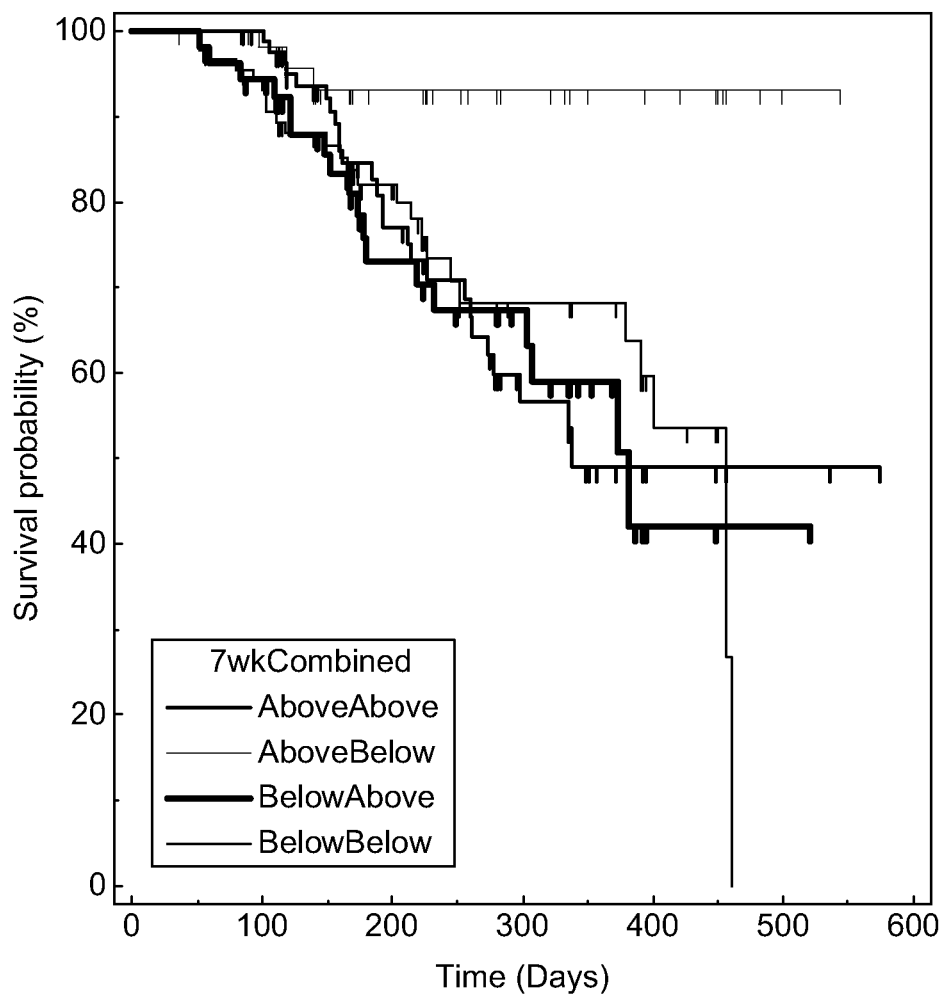
FIG. 2: Survival of TRIST patients stratified by 5T4 or MVA antibody response category (week 7).

For illustrative purposes, the following results detail 5T4 and MVA antibody responses at week 7 (similar analyses have been performed at week 10 and show a similar pattern). FIG. 2 plots the survival of TRIST patients which have been categorized by their 5T4 and MVA antibody responses at week 7. Table 4 summarizes the specifics of the four groups analyzed in FIG. 2.

TABLE 4

| Group | AboveAbove >Median 5T4 >Median MVA | AboveBelow >Median 5T4 <Median MVA | BelowAbove <Median 5T4 >Median MVA | BelowBelow <Median 5T4 <Median MVA |
|---|---|---|---|---|
| Sample Size | 85 | 56 | 53 | 89 |
| Median OS (Days) | 337 | Not Reached | 381 | 456 |
| Log-Rank | | 0.008 | | |

Conclusions

These data suggest that there is differential risk-benefit to patient survival dependent on the relative magnitudes of tumor antigen specific (5T4) and vector specific (MVA) antibody responses. Within this patient cohort a "relatively" high 5T4-specific antibody response in the presence of a "relatively" weak MVA-specific response appears to be favorable for enhanced survival. These data can be used to plan treatment strategies to maximize the survival advantage of 5T4 targeted immunotherapies.

Such strategies may comprise:
Use of prime boost approaches to minimize responses to viral vector whilst focusing boosting on the target antigen e.g., using combinations of vectors, 5T4 protein components.
MVA tolerization strategies
Identifying patient characteristics that would predict this type of response through assessment of baseline status
Altering dosing level, schedule, frequency Example 3

Further Analysis of Immune Response to 5T4

Figure 3:
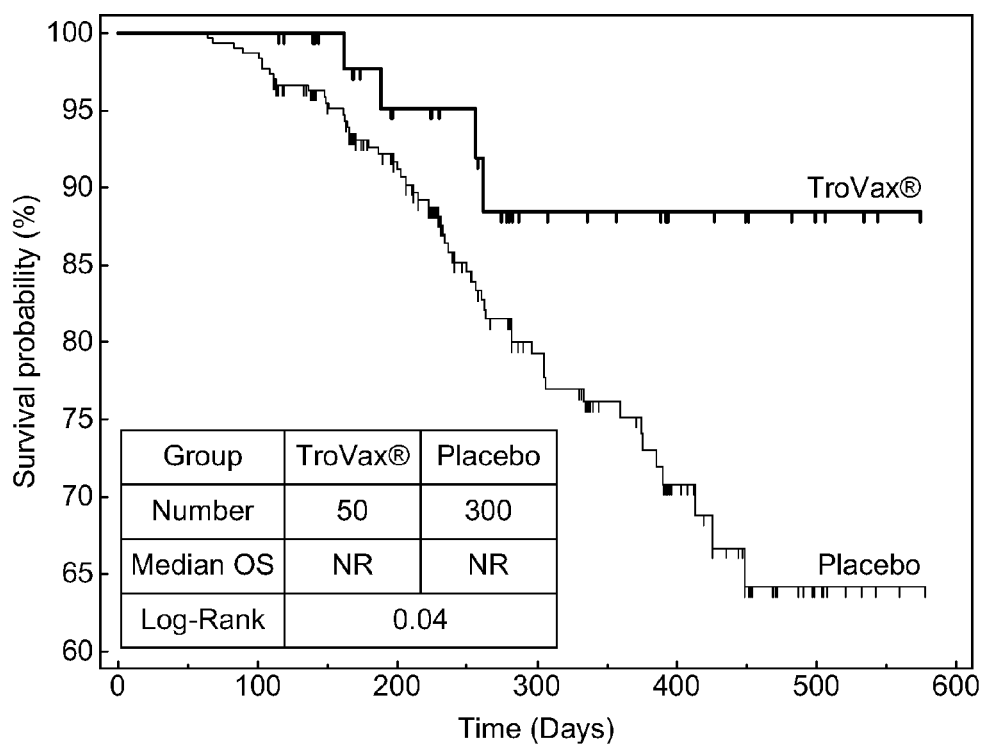
FIG. 3: Graph plots the survival of TroVax® (TRIST) patients (percent of total surviving patients in the trial over time) who show a greater than 4-fold increase in 5T4 antibody at week 10 relative to baseline. The 50 treated patients include 39 IFN patients, 9 IL-2 patients and 2 Sutent® (sunitinib malate) patients. The placebo arm includes all patients who were analyzed for antibody levels up to week 10 (i.e. had survived for at least 10 weeks).

TRIST study data was analyzed to determine whether significant 5T4 immune response in treated subjects correlated with patient survival. Increase in 5T4 antibody response (titer) relative to baseline was determined at 10 weeks (i.e., after the $4^{th}$ injection of MVA 5T4, TroVax®). Of 50 analyzed patients having a greater than 4-fold increase in 5T4 antibody levels, 39 were in the IFN group, 9 were IL-2 patients and 2 were Sutent® (sunitinib malate) patients. The survival of the patients demonstrating a 4-fold or greater increase (above baseline) in 5T4 antibody levels was plotted and compared to the survival of all patients receiving placebo (FIG. 3). Results of the analysis show that patients with elevated (greater than 4-fold) 5T4 antibody levels had a significantly enhanced survival rate relative to patients in the placebo treatment group.

Figure 4:
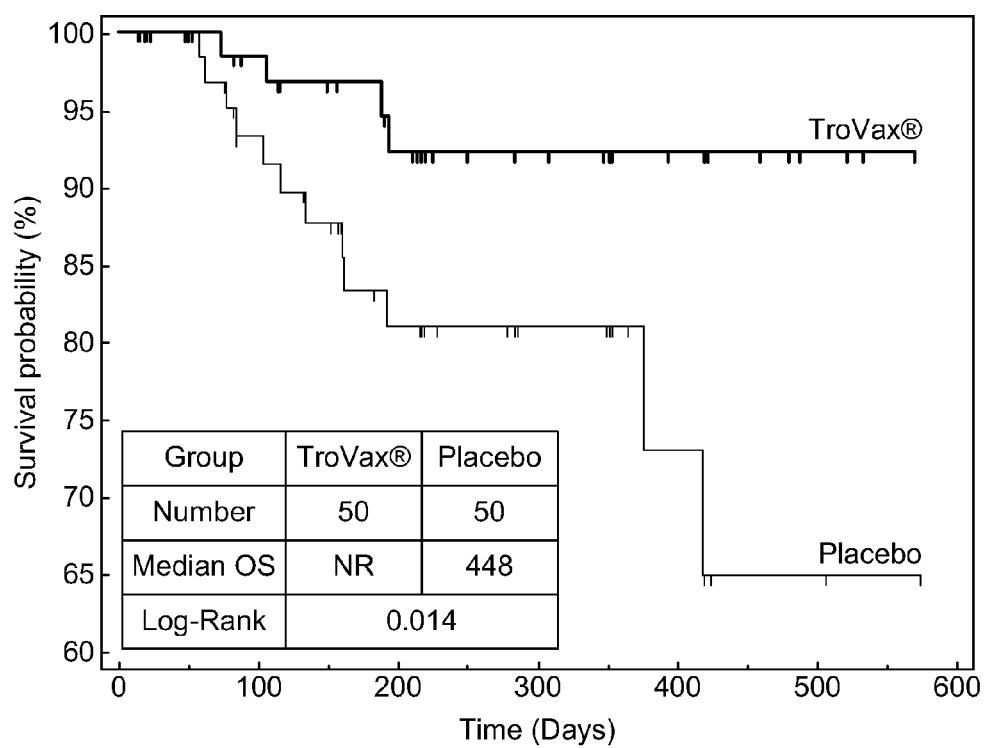
FIG. 4: Graph plots the survival of TroVax® (TRIST) patients (percent of total surviving patients in the trial over time) who show a greater than 4-fold increase in 5T4 antibody at week 10 relative to baseline. These 50 patients include 39 IFN patients, 9 IL-2 patients and 2 Sutent® (sunitinib malate) patients. The placebo arm has been matched to include the same numbers of SOCs and has selected those who have the largest fold-increase in 5T4 antibody at week 10.

Further analysis of patient survival was performed by comparing the 50 patients having a 4-fold increase in 5T4 antibody levels with an equal number of patients from the placebo group. The 50 selected placebo group patients were those that demonstrated the largest fold-increase in 5T4 antibody at week 10. The results of this analysis are shown in FIG. 4. A significant increase in survival rate was demonstrated for patients having a 4-fold increase in 5T4 antibody levels relative to the placebo group.

Example 4

Cross-Trial Analysis of Immunological and Clinical Data from Four Phase I and II Trials of MVA-5T4 in Colorectal Cancer Patients MVA-5T4 has been tested in one Phase I/II and three Phase II clinical trials in colorectal cancer patients, as described herein. Patients with histologically proven colorectal cancer (CRC) were recruited to 4 independent trials in which 3 to 6 vaccinations of MVA-5T4 were scheduled to be administered either as a monotherapy, as adjuvant/neo-adjuvant to surgery for resectable liver metastases or alongside treatment with FOLFIRI or FOLFOX. Antibody responses specific for 5T4 and MVA were monitored by ELISA. Survival data were collated from each hospital site. Immunological and survival data were analyzed using proportional hazards regression and adjusting for age and gender.

All trials demonstrated that MVA-5T4 was well tolerated when administered alone (1 trial), as adjuvant/neo-adjuvant to surgery (1 trial) or in combination with chemotherapy (FOLFOX or FOLFIRI; 2 trials).

Data accrued from the four Phase I and II trials (see Harrop et al. (2006) Clinical Cancer Research 12(11):3416-3424; Harrop et al. (2008) Cancer Immunol. Immunother. 57(7): 977-986; Harrop et al. (2007) Clinical Cancer Research 13(15):4487-4494; Elkord et al. (2008) J. Immunother. 31:820-829) of MVA-5T4 (TroVax®) in colorectal cancer patients were collated to determine the incidence of immune responses across trials and to look for associations with improved survival. Cellular and humoral responses were monitored against the tumor antigen 5T4 and the MVA viral vector.

Blood samples for immuno-monitoring were taken 1 or 2 weeks following each vaccination, with the maximum number of vaccinations administered per trial ranging from 5 to 6. Analysis of immunological and clinical responses on a per trial basis demonstrated statistically significant correlations between 5T4 (but not MVA) specific immune responses and clinical benefit in 3 of the 4 clinical trials.

5T4 and MVA-specific antibody responses and survival data were analyzed from 73 colorectal cancer patients (see Table 5, below).

TABLE 5

| CHARACTERISTICS | Trial | | | | |
|---|---|---|---|---|---|
| | Ph I/II | FOLFIRI | FOLFOX | Adjuvant | All Colorectal |
| Number of Patients | 22 | 19 | 17 | 20 | 73* |
| Age (Median) | 63 | 63 | 59 | 67 | 63 |
| Male | 17 | 13 | 11 | 14 | 50 |
| Female | 5 | 6 | 6 | 6 | 23 |
| Median Vaccinations (Range) | 4 (3-5) | 6 (1-6) | 6 (1-6) | 5 (2-6) | 5 (1-6) |
| Number of Vaccinations (Total) | 71 | 86 | 80 | 96 | 333 |

Figure 5A:
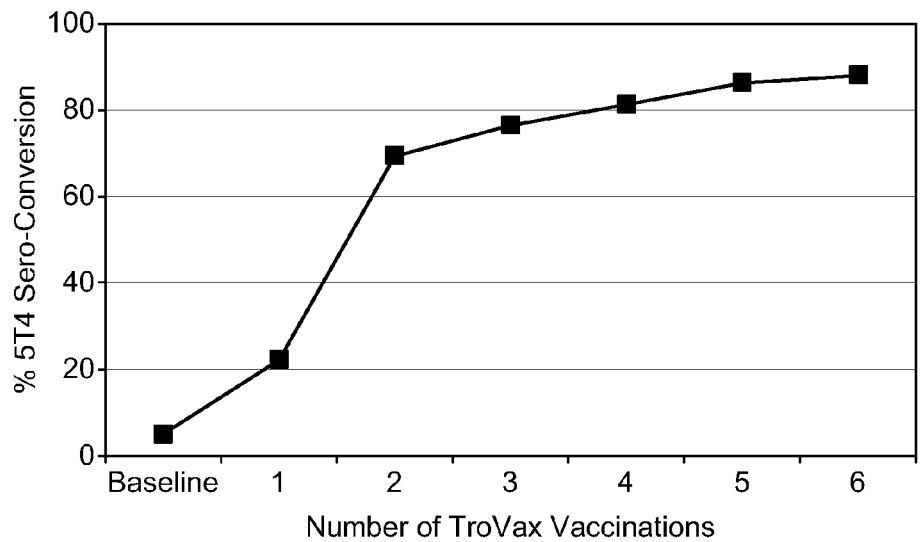
FIG. 5: (A) shows cross-trial analysis of the cumulative 5T4 sero-conversion following MVA-5T4 vaccination. (B) shows cross-trial analysis of 5T4 antibody titers in colorectal cancer patients.

To carry out cross-trial analysis of the cumulative 5T4 sero-conversion following MVA-5T4 vaccination, 5T4 antibody responses were assessed in 59 immunologically evaluable patients (Ph I/II (17 patients); FOLFIRI (12 patients); FOLFOX (11 patients); Adjuvant (19 patients)) following MVA-5T4 vaccination. The cumulative 5T4 sero-conversion rate was assessed by calculating the percentage of patients who had mounted a positive 5T4 antibody response following each vaccination (FIG. 5A).

Results showed that 5% of patients had detectable (low-level) 5T4 antibody responses present at baseline, while the majority of patients sero-converted following 2 MVA-5T4 vaccinations. In total, 88% of patients treated with MVA-5T4 mounted 5T4-specific antibody responses.

Next, a cross-trial analysis of 5T4 antibody titers in colorectal cancer patients was conducted. Here, 5T4 antibody titers were assessed in 59 immunologically evaluable patients (see above) at baseline (pre-vaccination) and 1-2wk following MVA-5T4 vaccination (up to a maximum of 6 vaccinations).

The associations are between the magnitude of the antibody response at single timepoints, post second or third injection. As this was a cross-trial analysis, the timing of the injections and the monitoring post-injection differed. The second and third injections occurred at the following times:

PhI/II (Harrop et al. (2006) Clinical Cancer Research 12(11):3416-3424): week 4 and week 8 with monitoring of antibody responses at wks 6 and 10.

FOLFIRI and FOLFOX (Harrop et al. (2008) Cancer Immunol. Immunother. 57(7):977-986 and Harrop et al. (2007) Clinical Cancer Research 13(15):4487-4494, respectively): injections at weeks 2 and 11 with antibody monitoring at weeks 4 and 13.

Adjuvant (Elkord et al. (2008) J. Immunother. 31:820-829): injections at weeks 2 and 8 with antibody monitoring at weeks 4 and 10.

Figure 5B:

FIG. 5B plots the mean 5T4 antibody titer following MVA-5T4 vaccination. The results showed that mean 5T4 antibody titers peaked following 2-3 MVA-5T4 vaccinations.

Analyses were undertaken to investigate whether the antibody responses induced by MVA-5T4 were associated with enhanced survival.

Figure 6:
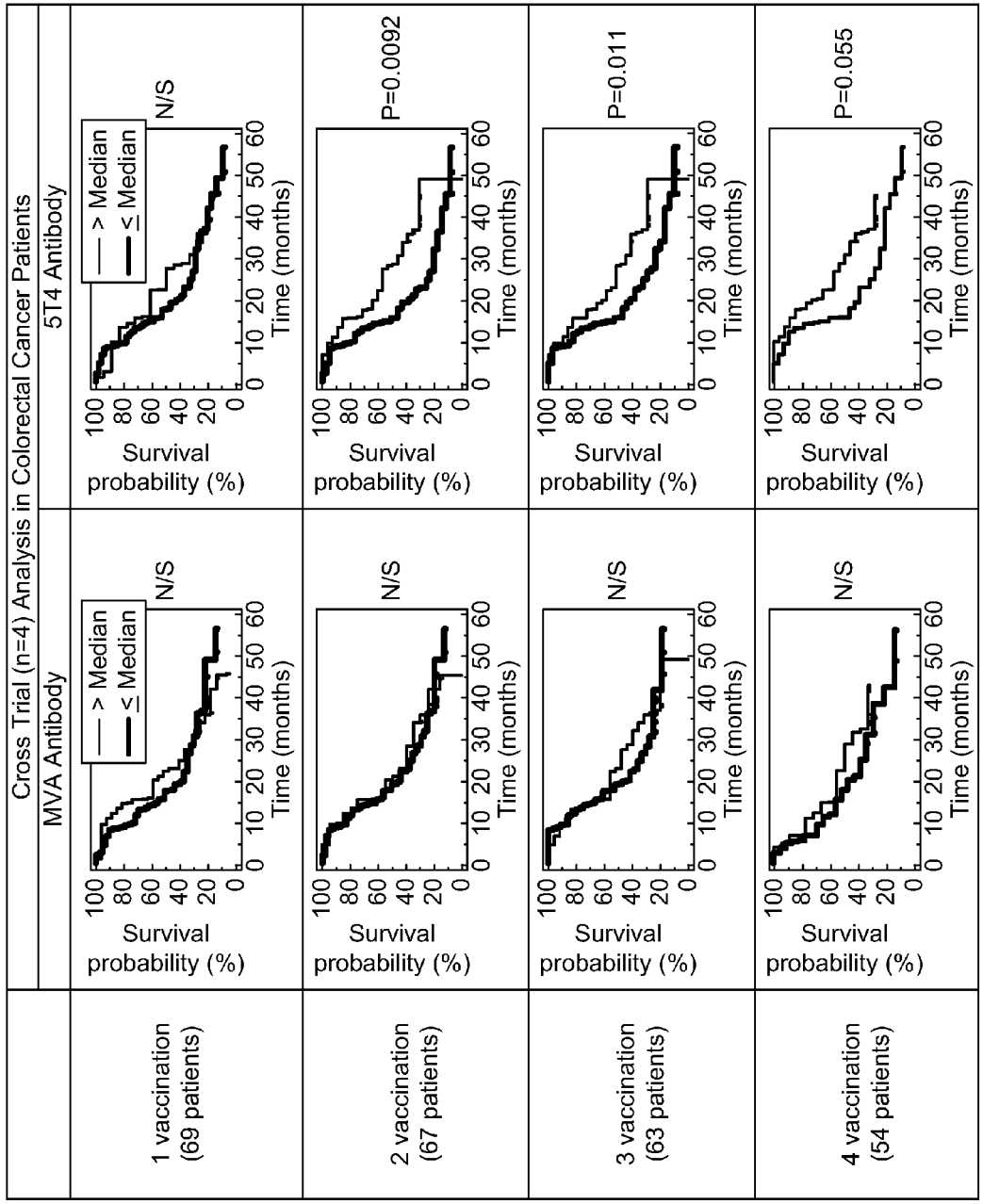
FIG. 6: Kaplan-Meier plots of survival over time for patients (see Example 5) who mounted above or below median MVA or 5T4 specific antibody responses are presented along with associated p-values.

A separate Cox proportional hazard model was fitted for each of the vaccinations with explanatory variables of i) the log of the antibody titer at the appropriate vaccination, ii) age and iii) gender. Kaplan-Meier plots for patients who mounted above or below median MVA or 5T4 specific antibody responses are presented along with associated p-values (Wald test). Results (FIG. 6) indicated that across 4 trials in CRC patients, Cox proportional hazards models that were adjusted for age and sex showed that a doubling in the 5T4 antibody titer at injection 2 was associated with a 14% reduction in relative risk of death (P<1%), and at injection 3 was associated with a 13% reduction in relative risk of death (P=1%) across the duration of the monitoring periods for the individual trials.

Also, 5T4, but not MVA, antibody responses are associated with enhanced patient survival across the four CRC trials. Further, for every doubling in 5T4 antibody response post 2nd MVA-5T4 vaccination, a reduction in relative risk of 14% was detected. An association between the magnitude of the 5T4 antibody response and enhanced patient survival was detected as early as post 2nd vaccination.

Example 5

Cross-Trial Analysis of Immunological and Clinical Data Resulting from Phase I and II Trials of MVA-5T4 (TroVax®) in Colorectal, Renal and Prostate Cancer Patients MVA-5T4 has been tested in two phase I/II and seven phase II clinical trials in colorectal (4 trials), renal (4 trials) and prostate (1 trial) cancer patients, as described herein. See also (Harrop et al. (2006) Clinical Cancer Research 12(11):3416: 3424; Harrop et al.

(2007) Clinical Cancer Research 13(15):4487-4494; Elkord et al. (2008) J. Immunother. 31:820-829; Amato et al. (2008) J. Immunother. 31:577-585; Amato et al. (2008) Clinical Cancer Research 14(22):7504-7510). All trials demonstrated that MVA-5T4 was well tolerated when administered alone (2 trials) or in combination with cytokines (5 trials) or chemotherapies (2 trials). Antibody and/or cellular responses specific for 5T4 were induced in the majority of patients and these responses were associated with clinical benefit in each of 6 trials. Data was collated from all nine TroVax® trials and the incidence and kinetics of immune responses was investigated across trials and associations with improved survival were noted.

Antibody responses specific for the 5T4 tumour antigen and the MVA viral vector were monitored by ELISA. Survival data were collated from each hospital site. Immunological and survival data were analyzed using proportional hazards regression adjusting for age and gender.

Blood samples for immuno-monitoring were taken 1 or 2 weeks following each vaccination. The maximum number of vaccinations administered per trial ranged from 5 to 12. 5T4 and MVA-specific antibody responses and survival data were analyzed from 189 colorectal, renal and prostate cancer patients, as described in Table 6 below.

TABLE 6

| | CANCER INDICATION | | | |
|---|---|---|---|---|
| CHARACTERISTICS | Colorectal | Renal | Prostate | TOTAL |
| Number of Patients | 73 | 89 | 27 | 189 |
| Age (Median) | 73 | 57 | 70 | 62 |
| Male | 50 | 63 | 27 | 140 (74%) |
| Female | 23 | 25 | 0 | 49 (26%) |
| Number of Vaccinations (Median) | 5 | 4 | 6 | 5 |

TABLE 6-continued

<table>
<tr><th rowspan="2">CHARACTERISTICS</th><th colspan="4">CANCER INDICATION</th></tr>
<tr><th>Colorectal</th><th>Renal</th><th>Prostate</th><th>TOTAL</th></tr>
<tr><td>Number of Vaccinations (Total)</td><td>333</td><td>476</td><td>161</td><td>970</td></tr>
</table>

5T4 Antibody responses were assessed in 180 patients who gave blood samples at baseline and at least one blood sample following a TroVax® vaccination. The cumulative 5T4 sero-conversion rate was assessed by calculating the percentage of patients who had mounted a positive 5T4 antibody response immediately (1-2 weeks) following one up to a maximum of twelve vaccinations (FIG. 7A).

Figure 7A:
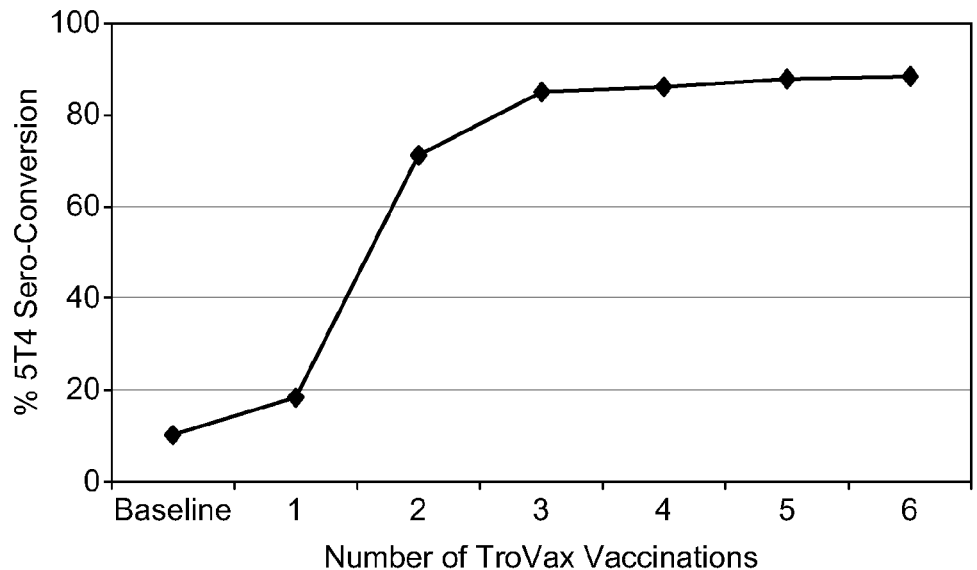
FIG. 7: (A) cross-trial analysis of the cumulative 5T4 sero-conversion rate following TroVax® vaccination. (B) cross-trial analysis of 5T4 antibody titers in (colorectal cancer) CRC, (renal clear cell adenocarcinoma) RCC and prostate cancer patients.

Results showed that 10% of patients had detectable (low-level) 5T4 antibody responses present at baseline, and also that the majority of patients sero-converted following 2 TroVax vaccinations (FIG. 7A). In total, 88% of patients treated with TroVax® (alone or in combination with chemo- or cytokine therapies) mounted a 5T4-specific antibody response.

5T4 antibody titers were also assessed in colorectal (4 trials; n=73 pts), renal (4 trials; n=81 pts) and prostate (1 trial; n=26 pts) cancer patients at baseline (pre-vaccination) and 1-2 wk following TroVax® vaccination (up to a maximum of 6).

Figure 7B:
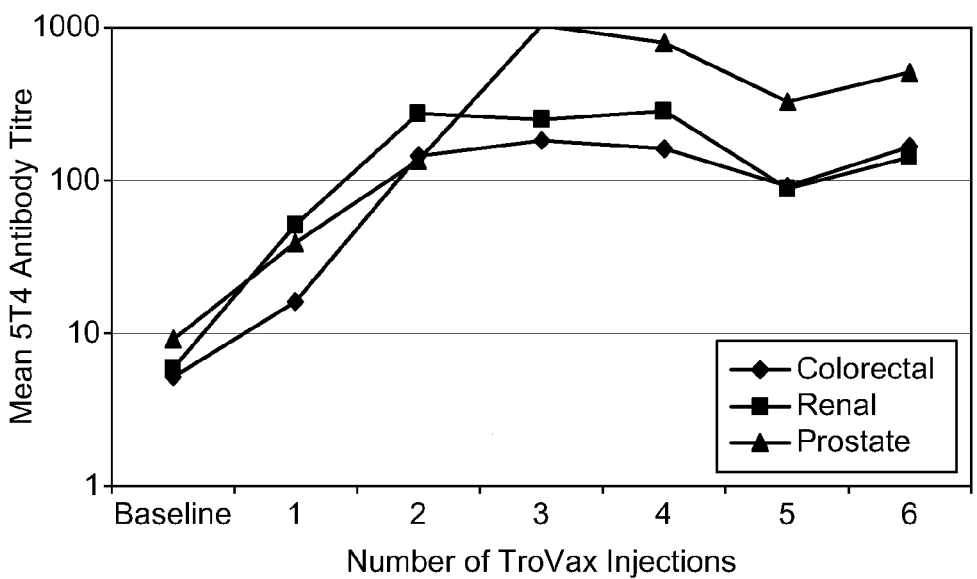
Figure 8:
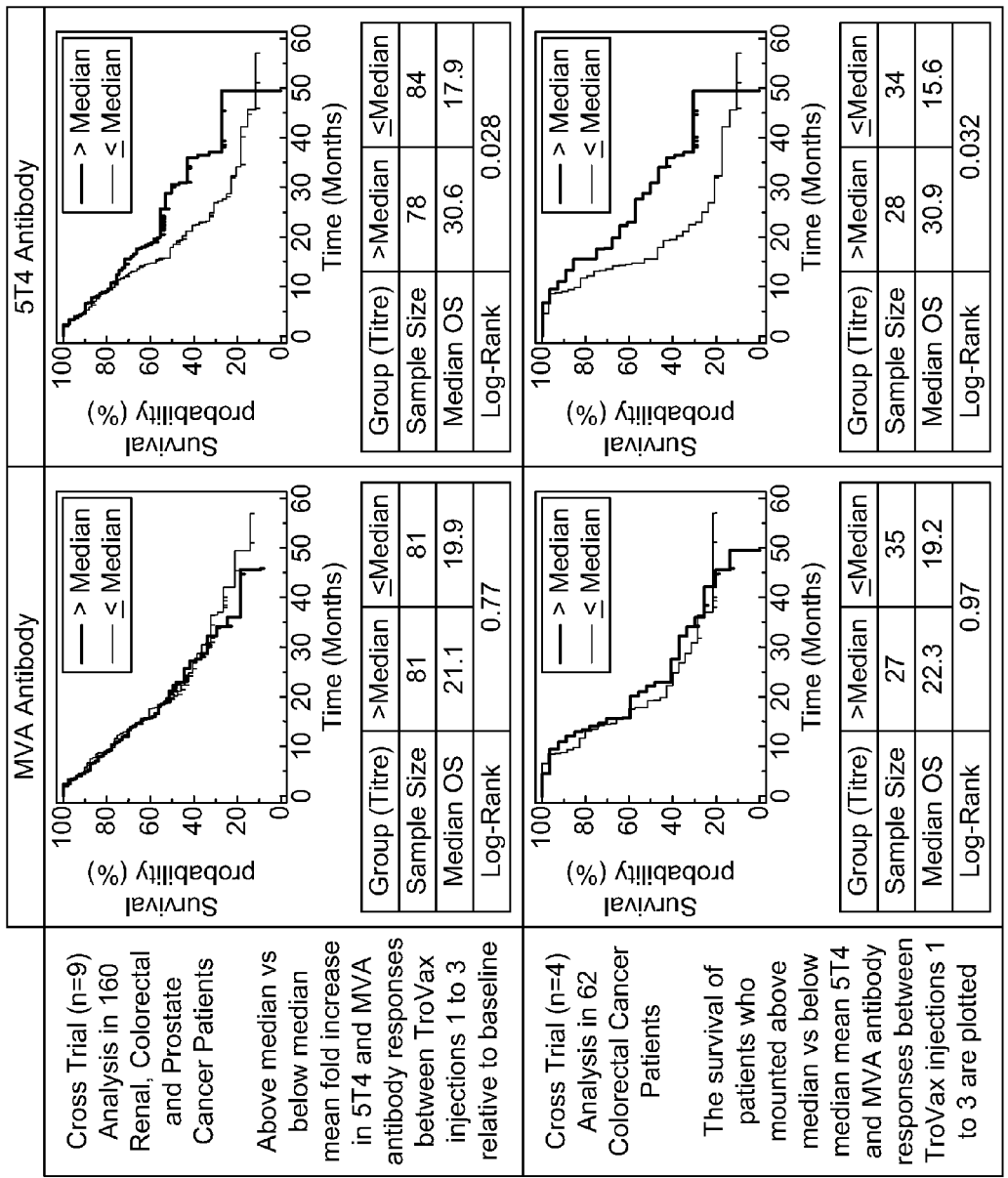
FIG. 8: Immunological responses versus survival. The survival of patients (see Example 7) who mounted above median or below median MVA or 5T4 specific antibody responses was compared using the log-rank test and depicted in Kaplan-Meier plots. (A) cross-trial analysis in 160 renal, colorectal and prostate cancer patients. (B) cross-trial analysis in 62 colorectal cancer patients.

FIG. 7B plots the mean 5T4 antibody titer following TroVax® vaccination in patients with colorectal, renal or prostate cancer. Results showed that the kinetics of the mean 5T4 antibody titer following TroVax® vaccination were similar across cancer indications despite differences in co-medications, vaccination regimen and disease characteristics. Mean 5T4 antibody titers peaked following 2-3 TroVax® vaccinations.

Following completion of the trials, the survival of patients who mounted above median or below median MVA or 5T4 specific antibody responses was compared using the log-rank test.

Results showed that across all 9 trials, a Cox proportional hazards model demonstrated that a doubling in the fold-increase of 5T4 antibody titer (injections 1 to 3 relative to baseline) was associated with a 16.3% reduction in relative risk of death over the course of the trials, adjusted for age and gender and stratified by indication (P<0.2%). Across 4 Trials in CRC Patients, a Cox proportional hazards model showed that a doubling in the geometric mean 5T4 antibody titer (injections 1 to 3) was associated with a 19.9% reduction in relative risk of death over the course of the trials, adjusted for age and gender (P<1%).

The studies described in Example 5 show that TroVax® induces 5T4-specific antibody responses in >80% colorectal, renal or prostate cancer patients when administered alone or in combination with chemo-or cytokine therapies. Also, the kinetics of the magnitude of 5T4 antibody responses is similar across indications despite the differences in co-meds, vaccination regimen and disease characteristics. The magnitude of the 5T4 (but not MVA) antibody response was shown to be associated with increased patient survival. Further, for every doubling in antibody response, a reduction in relative risk of death of 16% across all 9 trials and 19% across the 4 colorectal studies was detected.

The invention claimed is:

1. A method of therapy for mammalian subjects having a tumor expressing 5T4, and that have received a first vaccination and a second vaccination of an immunotherapy that comprises a modified vaccinia Ankara (MVA) viral vector containing a polynucleotide encoding 5T4 antigen, wherein the viral vector is capable of transducing cells in the mammalian subject to cause the cells to express the 5T4 antigen, the method comprising:
    (a) evaluating the subjects after the second vaccination and before any third vaccination by
        (i) measuring, from a biological sample isolated from the subjects, an antibody response of the subject to the 5T4 antigen and comparing the antibody response of the subjects to the 5T4 antigen to a reference measurement of antibody response to the 5T4 antigen; and
        (ii) measuring, from a biological sample isolated from the subjects, an antibody response of the subject to the viral vector and comparing the antibody response of the subjects to the viral vector to a reference measurement of antibody response to the viral vector; and
    (b) continuing the immunotherapy in a subject having an elevated antibody response to the 5T4 antigen and a reduced antibody response to the viral vector with at least a third vaccination of the immunotherapy; and discontinuing the immunotherapy and administering a secondary therapy to a subject lacking the elevated antibody response to the antigen or lacking the reduced antibody response to the viral vector, wherein the secondary therapy is selected from the group consisting of a chemotherapy, a radiotherapy, and a surgical therapy.

2. The method according to claim 1, wherein the reference measurement of antibody response to the antigen is an average or median measurement calculated from a plurality of mammalian subjects to whom the immunotherapy has been administered.

3. The method according to claim 1, wherein the reference measurement of antibody response to the viral vector is an average or median measurement calculated from a plurality of mammalian subjects to whom the immunotherapy has been administered.

4. The method according to claim 1, wherein a measurement for the mammalian subject above the reference measurement is scored as elevated, and a measurement below the reference measurement is scored as reduced.

5. The method according to claim 1, further comprising administering 5T4 antigen following cessation of administrations of the viral vector containing the polynucleotide encoding 5T4 antigen, to maintain or enhance the antibody response of the subject to 5T4 antigen.

6. The method according to claim 1, wherein the cancer is renal cancer.

7. The method according to claim 1, wherein the cancer is colorectal cancer.

8. The method according to claim 1, wherein the mammalian subject is human.

* * * * *